United States Patent
Chen et al.

(10) Patent No.: US 12,215,319 B2
(45) Date of Patent: Feb. 4, 2025

(54) METHODS AND COMPOSITIONS FOR TARGETED GENOMIC INSERTION

(71) Applicant: SYNGENTA PARTICIPATIONS AG, Basel (CH)

(72) Inventors: Zhongying Chen, Research Triangle Park, NC (US); Mary-Dell Chilton, Research Triangle Park, NC (US); Shujie Dong, Research Triangle Park, NC (US); Qiudeng Que, Research Triangle Park, NC (US); Heng Zhong, Research Triangle Park, NC (US)

(73) Assignee: Syngenta Crop Protection AG, Basel (CH)

( * ) Notice: Subject to any disclaimer, the term of this patent is extended or adjusted under 35 U.S.C. 154(b) by 1004 days.

(21) Appl. No.: 16/634,215

(22) PCT Filed: Jul. 26, 2018

(86) PCT No.: PCT/US2018/043855
§ 371 (c)(1),
(2) Date: Jan. 27, 2020

(87) PCT Pub. No.: WO2019/027789
PCT Pub. Date: Feb. 7, 2019

(65) Prior Publication Data
US 2021/0087557 A1 Mar. 25, 2021

Related U.S. Application Data

(60) Provisional application No. 62/541,219, filed on Aug. 4, 2017.

(51) Int. Cl.
*C12N 15/113* (2010.01)
*C12N 9/22* (2006.01)
*C12N 15/10* (2006.01)
*C12Q 1/68* (2018.01)

(52) U.S. Cl.
CPC .............. *C12N 15/113* (2013.01); *C12N 9/22* (2013.01); *C12N 15/102* (2013.01); *C12N 2310/20* (2017.05)

(58) Field of Classification Search
CPC ...... C12N 15/113; C12N 9/22; C12N 15/102; C12N 2310/20
See application file for complete search history.

(56) References Cited

U.S. PATENT DOCUMENTS

2016/0208243 A1   7/2016   Zhang et al.
2017/0051276 A1   2/2017   May et al.

FOREIGN PATENT DOCUMENTS

WO   2016/205613 A1   12/2016
WO   2017064546 A1   4/2017

OTHER PUBLICATIONS

Extended ESR for EP18840822.3, mailed on Mar. 19, 2021.
Qiudeng, Que et al.: "Maize transformation technology development for commercial event generation" in: Frontiers in Plant Science, vol. 5, Aug. 5, 2014, XP055217826, DOI: 10.3389/fpls.2014.00379.
International Search Report for PCT Application No. PCT/US2018/043855 mailed Nov. 20, 2018.

*Primary Examiner* — Sean McGarry
(74) *Attorney, Agent, or Firm* — Dale Skalla

(57) ABSTRACT

The present invention relates to methods and compositions for chimeric RNA comprising a guide RNA and bait RNA for modifying a target site in the genome of a cell. Such modifications include integration of a transgene and allelic mutations and modifications of native genes. Also provided are plants comprising a modified nucleic acid sequence compared to the native gene integrated into a targeted genomic site in the plant genome.

9 Claims, 2 Drawing Sheets

Specification includes a Sequence Listing.

Use of sequence of interest (SOI)-specific bait

I) Use of sequence of interest (SOI)-specific bait a) Chimeric gRNA with bait RNA segment fused to gRNA

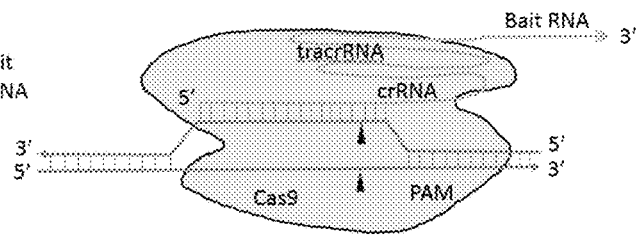

b) Chimeric guide RNA guided target cleavage and recruitment of donor DNA

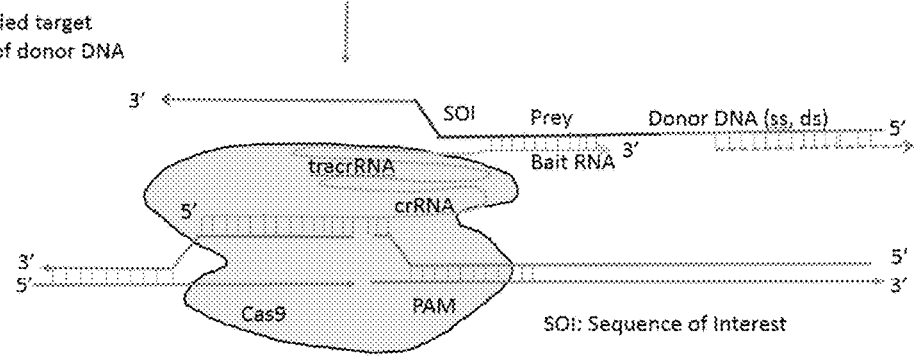

c) Strand invasion by donor at the break of cleaved target

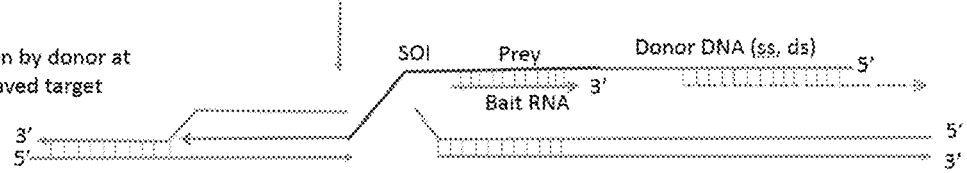

d) Extension of annealed strand

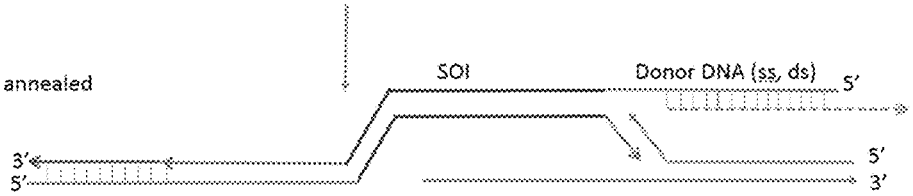

e) Flap removal, gap filling and ligation

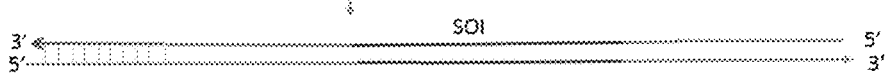

Recombinant product with desirable sequence of interest (SOI)

FIG. 1

Use of universal bait sequence

II) Use of universal bait design a) Chimeric gRNA with universal bait RNA fused to gRNA

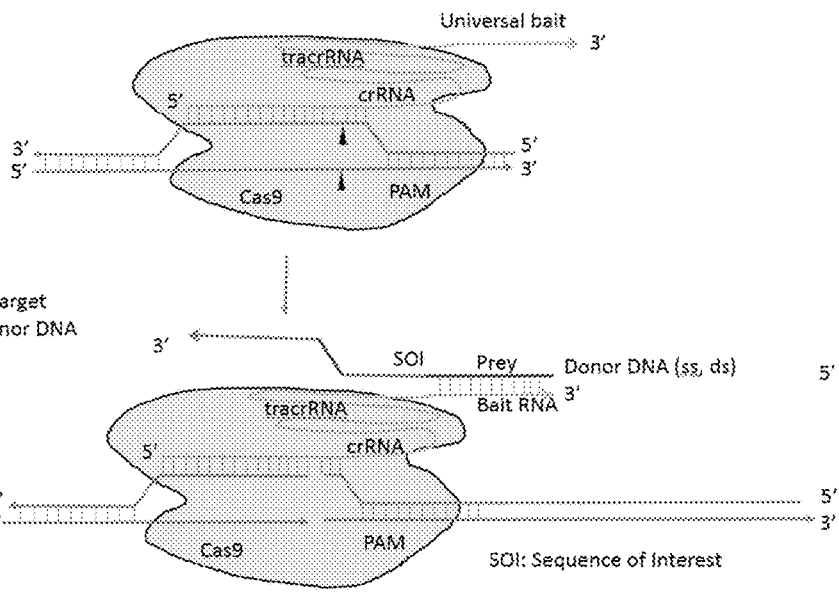

b) Chimeric guide RNA guided target cleavage and recruitment of donor DNA

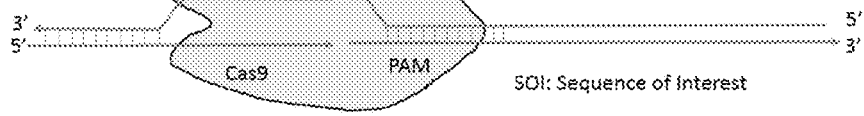

c) Strand invasion by donor at the break of cleaved target

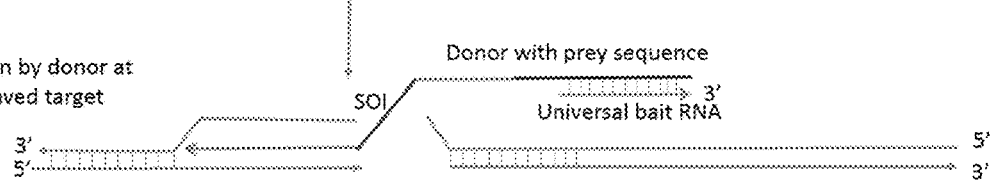

d) Extension of annealed strand

e) Flap removal, gap filling and ligation

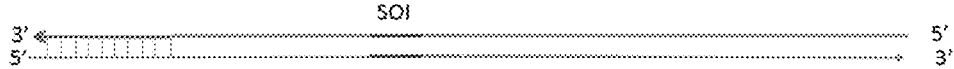

Recombinant product with desirable sequence of interest (SOI)

FIG. 2

METHODS AND COMPOSITIONS FOR TARGETED GENOMIC INSERTION

CROSS REFERENCE TO RELATED APPLICATIONS

This application is a 371 of International Application No. PCT/US2018/043855, filed Jul. 26, 2018 which claims the benefit of U.S. Provisional Patent Application No. 62/541,219 filed Aug. 4, 2017, the contents of which are incorporated by reference in their entirety.

SEQUENCE LISTING

A Sequence Listing in ASCII text format, submitted under 37 C.F.R. § 1.821, entitled "81321PCT_ST25.txt", 29 kilobytes in size, generated on Jul. 17, 2018 and filed via EFS-Web is provided in lieu of a paper copy. This Sequence Listing is hereby incorporated by reference into the specification for its disclosures.

FIELD OF THE INVENTION

The present invention relates to methods and compositions for targeted transgene insertion or targeted allelic replacement in the genome of a cell.

BACKGROUND OF THE INVENTION

Significant advances have been made in the last few years towards the development of methods and compositions to target and cleave genomic DNA by site specific nucleases (e.g., Zinc Finger Nucleases (ZFNs), Meganucleases, Transcription Activator-Like Effector Nucleases (TALENS) and Clustered Regularly Interspaced Short Palindromic Repeats/ CRISPR-associated nuclease (CRISPR/Cas) with an engineered crRNA/tracr RNA), to induce targeted mutagenesis, induce targeted deletions of DNA sequences, and facilitate targeted recombination of an exogenous donor DNA polynucleotide, such as a transgene, within a predetermined genomic locus. The application of site-directed nucleases (SDNs)-mediated targeted insertion technology for trait improvement has been demonstrated in several field crops, including tobacco (Cai et al, 2009. Plant Mol Biol, 69:699-709), cotton (Dhalluin et al, 2013. Plant Biotechnology Journal, 11: 933-941) and maize (Dhalluin et al, 2008. Plant Biotechnology Journal, 6: 93-102; Ainley et al, 2013. Plant Biotechnology Journal, 11: 1126-1134).

Successful insertion of an exogenous donor DNA molecule to a targeted genomic locus remains difficult, however. A high percentage of these targeted insertion events contain at least one end repaired by the Non-Homologous End Joining (NHEJ) process, which allows for the insertion of multiple donor DNA fragments in multiple orientations and does not result in a predictable and precise junction sequence connecting these donor DNA fragments with the target locus. The low frequency of precise targeted insertion generated by double crossover homologous recombination (HR) remains to hinder the full deployment of the technology in a routine event generation pipeline. Therefore, there is a need in the art to develop methods that increase targeted insertion frequency, both for transgene insertion and for allelic replacement via recombination. The present invention addresses these shortcomings in the art by providing improved methods and compositions for genomic modifications of a cell.

SUMMARY OF THE INVENTION

The present invention provides an engineered chimeric RNA, which comprises a guide RNA and a "bait" RNA. The guide RNA may be operably linked to the bait RNA. The guide RNA comprises a crRNA segment, which comprising a guide sequence capable of hybridizing to a target sequence and a stem sequence that is capable of binding to a site-directed modifying polypeptide. The guide RNA may be a single RNA molecule or more than one RNA molecule. The guide RNA may also comprise a tracrRNA segment comprising a nucleic acid sequence that is capable of interacting with the crRNA. The bait RNA segment comprises at least 8 nucleotides, wherein the nucleic acid sequence of the bait segment is complementary to at least 8 nucleic acids of a donor DNA molecule and is capable of hybridizing to the donor DNA molecule, wherein the donor DNA molecule is intended for integration into the genome of a cell. The present invention further provides an engineered chimeric RNA comprising a crRNA segment comprising a guide sequence capable of hybridizing to a genomic target sequence, a CRISPR repeat or crRNA scaffold sequence, and a bait RNA segment capable of hybridizing to a donor DNA molecule. The present invention further provides methods for targeted transgene insertion into a target genomic site of a cell, and further provides methods for targeted allelic replacement by nucleic acid modification of a target genomic site in a cell. Schematic drawings in FIGS. 1 and 2 illustrate the use of a chimeric RNA, comprising a guide RNA and a bait RNA, for donor recruitment.

The present invention further provides a chimeric RNA which comprises more than one RNA molecule. The chimeric RNA may be a dual guide RNA, which may comprise a crRNA linked to a bait RNA and a tracrRNA molecule, for example, or a tracrRNA linked to a bait RNA and a crRNA, for example. The present invention further provides at least one nucleic acid molecule that comprises a nucleic acid sequence encoding the chimeric RNA, which comprises a guide RNA and a bait RNA.

In one aspect, the present invention provides a method of targeted integration of a transgene into a target genomic site of a cell, comprising introducing into the cell: a) a first nucleic acid molecule comprising a donor DNA molecule comprising a transgene, and further comprising at least 10 contiguous nucleic acids which are at least 80% identical to a genomic nucleic acid sequence, and b) a second nucleic acid molecule comprising a nucleotide sequence encoding a site-directed modifying polypeptide capable of site-directed cleavage at the target genomic site proximal to the genomic nucleic acid sequence of part a), and further comprising at least one nucleic acid sequence encoding the chimeric RNA of the invention, wherein the target nucleic acid sequence is a target genomic site of the cell, under conditions wherein expression of the second nucleic acid molecule can occur to produce the site-directed polypeptide and the site-directed polypeptide can cleave the nucleotide sequence at the target genomic site, whereby the transgene is integrated at the target genomic site in the genome of the cell.

The invention further provides a method of targeted integration of a transgene into a target genomic site of a cell, comprising providing to the cell: a) a first nucleic acid molecule comprising a donor DNA molecule comprising a transgene, and further comprising at least 10 contiguous nucleic acids which are at least 80% identical to a genomic nucleic acid sequence, b) a second nucleic acid comprising at least one nucleic acid sequence comprising a chimeric RNA of the invention, wherein the target nucleic acid sequence is a target genomic site of the cell, and c) a site-directed polypeptide capable of site-directed cleavage at the target genomic site proximal to the genomic nucleic acid sequence of part a), under conditions wherein the site-directed polypeptide can cleave the targeted genomic nucleotide sequence at the target genomic site, whereby the transgene is integrated at the target genomic site in the genome of the cell.

The invention further provides the methods of targeted integration of a transgene into a target genomic site of a cell described above, where the methods are an improvement with higher targeted integration efficiency compared to methods where the guide RNA is not a chimeric RNA comprising a guide RNA and a bait RNA. The invention further provides these methods described above, where the bait RNA is at least 8 contiguous nucleic acids and is at least 70% complementary to a fragment of the donor molecule. This fragment may be to the transgene, to the genomic nucleic acid sequence, or to a region of the donor molecule which is neither of these.

The invention also provides a method of allelic replacement by nucleic acid modification of a target genomic site in a cell, whereby the target genomic site comprises at least a fragment of a native gene, comprising introducing into the cell: a) a first nucleic acid molecule comprising a donor DNA molecule comprises a modified nucleic acid molecule comprising a nucleic acid sequence modified compared to the native gene, and said donor DNA molecule further comprising at least 10 contiguous nucleotides at least 80% identical to a genomic nucleic acid sequence, and b) a second nucleic acid molecule comprising a nucleotide sequence encoding a site-directed modifying polypeptide capable of site-directed cleavage at the target genomic site proximal to the genomic nucleic acid sequence of part a), and further comprising at least one nucleic acid sequence encoding a chimeric RNA of the invention, wherein the target nucleic acid sequence is the target genomic site of the cell, under conditions wherein expression of the second nucleic acid molecule can occur to produce the site-directed modifying polypeptide and the site-directed modifying polypeptide can cleave the nucleotide sequence of the target genomic site, whereby the modified nucleic acid molecule is integrated at the target genomic site in the genome of the cell, thereby producing an allelic replacement.

The invention further provides a method of allelic replacement by nucleic acid modification of a target genomic site in a cell, whereby the target genomic site comprises at least a fragment of a native gene, comprising providing to the cell: a) a first nucleic acid molecule comprising a donor DNA molecule comprising a modified nucleic acid molecule comprising a nucleic acid sequence modified compared to the native gene, and said donor DNA molecule further comprising at least 10 contiguous nucleotides at least 80% identical to a genomic nucleic acid sequence, b) a second nucleic acid molecule comprising at least one nucleic acid sequence comprising a chimeric RNA of the invention, wherein the target nucleic acid sequence is the target genomic site of the cell, and c) a site-directed modifying polypeptide capable of site-directed cleavage at the target genomic site proximal to the genomic nucleic acid sequence of part a), under conditions wherein the site-directed modifying polypeptide can cleave the nucleotide sequence of the target genomic site, whereby the modified nucleic acid molecule is integrated at the target genomic site in the genome of the cell, thereby producing an allelic replacement.

The invention further provides the methods of allelic replacement by nucleic acid modification of a target genomic site in a cell described above, where the methods are an improvement with higher targeted integration efficiency compared to methods where the guide RNA is not a chimeric RNA comprising a guide RNA and a bait RNA. The invention further provides these methods described above, where the bait RNA is at least 8 contiguous nucleic acids and is at least 70% complementary to a fragment of the donor molecule. This fragment may be to the modified nucleic acid molecule comprising a nucleic acid sequence modified compared to the native gene, to the genomic nucleic acid sequence, or to a region of the donor molecule which is neither of these.

The invention further provides methods of targeted transgene insertion or allelic replacement, where the nucleic acid molecules introduced into the cell are present on a single nucleic acid construct or are present on separate nucleic acid constructs. The invention further provides that a nucleic acid molecule which encodes a site-directed modifying polypeptide and/or which encodes a chimeric RNA of the invention may be transiently expressed in a cell.

The invention further provides the methods of targeted transgene insertion or allelic replacement described above, where the donor DNA molecule is single-stranded or is at least partially double-stranded. The invention further provides said methods where the site-directed modifying polypeptide is an RNA-guided nuclease, or further described as a CRISPR-associated nuclease. The invention further provides said methods where a nucleic acid molecule comprising a nucleotide sequence encoding an anti-silencing polypeptide is introduced into the cell. The invention further provides said methods where an anti-silencing polypeptide is provided to the cell.

The invention further provides the methods of targeted transgene insertion or allelic replacement described above, where the cell is a plant cell. The plant cell may be conifer plant cell, a monocotyledonous plant cell, or a dicotyledonous plant cell. The plant cell may be a maize, rice, sorghum, sugarcane, barley, wheat, oat, turf grass, ornamental grass, tobacco, tomato, pepper, eggplant, sunflower, crucifer, flax, potato, cotton, soybean, sugar beet, or oilseed rape cell. The invention further provides methods of targeted transgene insertion or allelic replacement described above, where the nucleic acid molecules are introduced into the plant cell by biolistic nucleic acid delivery or by *Agrobacterium*-mediated transformation.

The present invention also provides a method of producing a plant, plant part, or progeny thereof comprising a transgene integrated into a targeted genomic site in the plant genome, comprising regenerating a plant from the cell produced by a method of targeted transgene insertion described above. The present invention further provides a plant, plant part, or progeny thereof comprising a transgene integrated into a targeted genomic site in the plant genome, produced by the method described.

The present invention also provides a method of producing a plant, plant part, or progeny thereof comprising a modified nucleic acid sequence compared to the native gene integrated into a targeted genomic site in the plant genome, comprising regenerating a plant from the cell produced by a method of allelic replacement described above. The present invention further provides a plant, plant part, or progeny thereof comprising a modified nucleic acid sequence compared to the native gene integrated into a targeted genomic site in the plant genome, produced by the method described.

BRIEF DESCRIPTION OF THE DRAWINGS

FIG. 1 is a schematic of the use of sequence of interest bait RNA.
FIG. 2 is a schematic of the use of a universal bait RNA.

BRIEF DESCRIPTION OF THE SEQUENCES IN THE SEQUENCE LISTING

SEQ ID NO: 1 is a nucleotide sequence of MIR604FR2, a maize genomic sequence that may be a target sequence for transgene insertion.
SEQ ID NO: 2 is a nucleotide sequence of xZmMIR604FR2, which corresponds to the genomic sequence of MIR604FR2, a maize genomic sequence.
SEQ ID NO: 3 is a nucleotide sequence of rsgRNAZmMIR604FR2, which encodes a single guide RNA.
SEQ ID NO: 4 is a nucleotide sequence of PMIRV, which is complementary to a fragment of the PMI gene and may encode a bait RNA.
SEQ ID NO: 5 is a nucleotide sequence of rsgRNAZmMIR604FR2PMI, which encodes a single guide RNA molecule of the invention, where the guide RNA molecule comprises a bait RNA.
SEQ ID NO: 6 is a nucleotide sequence of xJHAX-03, a maize genomic sequence.
SEQ ID NO: 7 is a nucleotide sequence of xJHAX-04, a maize genomic sequence.
SEQ ID NO: 8 is a nucleotide sequence comprising the expression cassette prUbi1-10: cBCas9Nu-01: tNOS-5-1.
SEQ ID NO: 9 is a nucleotide sequence comprising the expression cassette prOsU3-01: xZmMIR604FR2: rsgRNAZmMIR604FR2.
SEQ ID NO: 10 is a nucleotide sequence comprising the expression cassette prOsU3-01: xZmMIR604FR2: rsgRNAZmMIR604FRxPMI.
SEQ ID NO: 11 is a nucleotide sequence comprising xJHAX-03: prUbi1-10: cPMI-09: tNOS-05-01: xJAX-04.
SEQ ID NO: 12-21 are nucleotide sequences for primers and probes useful for the detection of a targeted insertion.
SEQ ID NO: 22 is a nucleotide sequence of a segment of the wild type maize Bx9 gene
SEQ ID NO: 23 is the amino acid sequence encoded by SEQ ID NO: 22.
SEQ ID NO: 24 is a nucleotide sequence of a targeting RNA to guide Cas9-mediated cleavage of Bx9 gene target
SEQ ID NO: 25 is a nucleotide sequence of a bait RNA segment
SEQ ID NO: 26 is a nucleotide sequence of a 108 bp donor oligonucleotide containing the intended A334K mutation and other synonymous mutations (in the coding strand and mutated nucleotides in lower case) to allow heteroduplex formation with bait RNA (SEQ ID NO: 25).
SEQ ID NO: 27 is a nucleotide sequence of a donor DNA molecule that contains 3 mutant nucleotides encoding the desired A334K mutations and additional silent mutations.
SEQ ID NO: 28 is a mutant peptide sequence encoded by SEQ ID NO: 27.
SEQ ID NO: 29 is a nucleotide sequence of universal bait xScAdh1 derived from yeast gene Adh1.
SEQ ID NO: 30 is a nucleotide sequence of guide RNA rsgRNAZmBx9-08.
SEQ ID NO: 31 is a nucleotide sequence of prey xScAdh1RV which is complementary to bait xScAdh1.
SEQ ID NO: 32 is a nucleotide sequence of mutant Bx9 gene sequence (the non-coding strand) containing 2 nucleotide mutations (GG to CT) allowing generation of A334K amino acid mutation.
SEQ ID NO: 33 is a nucleotide sequence of a chimeric donor sequence containing the prey sequence of SEQ ID NO: 31, operably linked to the 5'-end of the mutant Bx9 sequence of SEQ ID NO: 32.

DETAILED DESCRIPTION OF THE INVENTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, and other references mentioned herein are incorporated by reference in their entirety.

The following definitions and methods are provided to better define the present invention and to guide those of ordinary skill in the art in the practice of the present invention. Unless otherwise noted, terms used herein are to be understood according to conventional usage by those of ordinary skill in the relevant art. Definitions of common terms in molecular biology may also be found in Rieger et al., *Glossary of Genetics: Classical and Molecular*, 5$^{th}$ edition, Springer-Verlag, New York, 1994.

As used in the description of the embodiments of the invention and the appended claims, the singular forms "a," "an," and "the" are intended to include the plural forms as well, unless the context clearly indicates otherwise.

As used herein, "and/or" refers to and encompasses any and all possible combinations of one or more of the associated listed items.

The term "about," as used herein when referring to a measurable value such as an amount of a compound, dose, time, temperature, and the like, is meant to encompass variations of 20%, 10%, 5%, 1%, 0.5%, or even 0.1% of the specified amount.

The terms "comprise," "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the term "amplified" means the construction of multiple copies of a nucleic acid molecule or multiple copies complementary to the nucleic acid molecule using at least one of the nucleic acid molecules as a template. See, e.g., Diagnostic Molecular Microbiology: Principles and Applications, D. H. Persing et al., Ed., American Society for Microbiology, Washington, D.C. (1993). The product of amplification is termed an amplicon.

A "coding sequence" is a nucleic acid sequence that is transcribed into RNA such as mRNA, rRNA, tRNA, snRNA, sense RNA or antisense RNA. In some embodiments, the RNA is then translated in an organism to produce a protein.

As used herein the term transgenic "event" refers to a recombinant plant produced by transformation and regeneration of a single plant cell with heterologous DNA, for example, an expression cassette that includes one or more genes of interest (e.g., transgenes). The term "event" refers to the original transformant and/or progeny of the transformant that include the heterologous DNA. The term "event" also refers to progeny produced by a sexual outcross between the transformant and another line. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. Thus, "event MIR604," "MIR604" or "MIR604 event" as used herein, means the original MIR604 transformant and/or progeny of the MIR604 transformant (U.S. Pat. Nos. 7,361,813, 7,897,748, 8,354,519, and 8,884,102, incorporated by references herein).

"Expression cassette" as used herein means a nucleic acid molecule capable of directing expression of a particular nucleotide sequence in an appropriate host cell, comprising a promoter operably linked to the nucleotide sequence of interest, typically a coding region, which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette may also comprise sequences not necessary in the direct expression of a nucleotide sequence of interest but which are present due to convenient restriction sites for removal of the cassette from an expression vector. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation process known in the art. The expression of the nucleotide sequence in the expression cassette may be under the control of a constitutive promoter or of an inducible promoter that initiates transcription only when the host cell is exposed to some particular external stimulus. In the case of a multicellular organism, such as a plant, the promoter can also be specific to a particular tissue, or organ, or stage of development. An expression cassette, or fragment thereof, can also be referred to as "inserted sequence" or "insertion sequence" when transformed into a plant.

A "gene" is a defined region that is located within a genome and that, besides the aforementioned coding nucleic acid sequence, comprises other, primarily regulatory, nucleic acid sequences responsible for the control of the expression, that is to say the transcription and translation, of the coding portion. Genes can include both coding and non-coding regions (e.g., introns, regulatory elements, promoters, enhancers, termination sequences and 5' and 3' untranslated regions). A gene typically expresses mRNA, functional RNA, or specific protein, including regulatory sequences. Genes may or may not be capable of being used to produce a functional protein. In some embodiments, a gene refers to only the coding region. The term "native gene" refers to a gene as found in nature. The term "chimeric gene" refers to any gene that contains 1) DNA sequences, including regulatory and coding sequences that are not found together in nature, or 2) sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature. A gene may be "isolated" by which is meant a nucleic acid molecule that is substantially or essentially free from components normally found in association with the nucleic acid molecule in its natural state. Such components include other cellular material, culture medium from recombinant production, and/or various chemicals used in chemically synthesizing the nucleic acid molecule.

By the term "express" or "expression" of a polynucleotide coding sequence, it is meant that the sequence is transcribed, and optionally translated.

A "gene of interest", "nucleotide sequence of interest", or "sequence of interest" refers to any gene which, when transferred to a plant, confers upon the plant a desired characteristic such as antibiotic resistance, virus resistance, insect resistance, disease resistance, or resistance to other pests, herbicide tolerance, improved nutritional value, improved performance in an industrial process or altered reproductive capability. The "gene of interest" may also be one that is transferred to plants for the production of commercially valuable enzymes or metabolites in the plant.

As used herein, "heterologous" refers to a nucleic acid molecule or nucleotide sequence not naturally associated with a host cell into which it is introduced, that either originates from another species or is from the same species or organism but is modified from either its original form or the form primarily expressed in the cell, including non-naturally occurring multiple copies of a naturally occurring nucleic acid sequence. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g., present in a different copy number, and/or under the control of different regulatory sequences than that found in the native state of the nucleic acid molecule. A nucleic acid sequence can also be heterologous to other nucleic acid sequences with which it may be associated, for example in a nucleic acid construct, such as e.g., an expression vector. As one non-limiting example, a promoter may be present in a nucleic acid construct in combination with one or more regulatory element and/or coding sequences that do not naturally occur in association with that particular promoter, i.e., they are heterologous to the promoter.

A "homologous" nucleic acid sequence is a nucleic acid sequence naturally associated with a host cell into which it is introduced. A homologous nucleic acid sequence can also be a nucleic acid sequence that is naturally associated with other nucleic acid sequences that may be present, e.g., in a nucleic acid construct. As one non-limiting example, a promoter may be present in a nucleic acid construct in combination with one or more regulatory elements and/or coding sequences that naturally occur in association with that particular promoter, i.e. they are homologous to the promoter.

"Operably-linked" refers to the association of nucleic acid sequences on a single nucleic acid sequence so that the function of one affects the function of the other. For example, a promoter is operably-linked with a coding sequence or functional RNA when it is capable of affecting the expression of that coding sequence or functional RNA (i.e. the coding sequence or functional RNA is under the transcriptional control of the promoter). Coding sequences in sense or antisense orientation can be operably-linked to regulatory sequences. Thus, regulatory or control sequences (e.g., promoters) operatively associated with a nucleotide sequence are capable of effecting expression of the nucleotide sequence. For example, a promoter operably linked to a nucleotide sequence encoding GFP would be capable of effecting the expression of that GFP nucleotide sequence.

The control sequences need not be contiguous with the nucleotide sequence of interest, as long as they function to direct the expression thereof. Thus, for example, intervening untranslated, yet transcribed, sequences can be present between a promoter and a coding sequence, and the promoter sequence can still be considered "operably linked" to the coding sequence.

"Primers" as used herein are isolated nucleic acids that are annealed to a complementary target DNA strand by nucleic acid hybridization to form a hybrid between the primer and the target DNA strand, then extended along the target DNA strand by a polymerase, such as DNA polymerase. Primer pairs or sets can be used for amplification of a nucleic acid molecule, for example, by the polymerase chain reaction (PCR) or other nucleic-acid amplification methods.

A "probe" is an isolated nucleic acid molecule that is complementary to a portion of a target nucleic acid molecule and is typically used to detect and/or quantify the target nucleic acid molecule. Thus, in some embodiments, a probe can be an isolated nucleic acid molecule to which is attached a detectable moiety or reporter molecule, such as a radioactive isotope, ligand, chemiluminescence agent, fluorescence agent or enzyme. Probes according to the present invention can include not only deoxyribonucleic or ribonucleic acids but also polyamides and other probe materials that bind specifically to a target nucleic acid sequence and can be used to detect the presence of and/or quantify the amount of, that target nucleic acid sequence.

A TaqMan probe is designed such that it anneals within a DNA region amplified by a specific set of primers. As the Taq polymerase extends the primer and synthesizes the nascent strand from a single-strand template from 3' to 5' of the complementary strand, the 5' to 3' exonuclease of the polymerase extends the nascent strand through the probe and consequently degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Primers and probes are generally between 5 and 100 nucleotides or more in length. In some embodiments, primers and probes can be at least 20 nucleotides or more in length, or at least 25 nucleotides or more, or at least 30 nucleotides or more in length. Such primers and probes hybridize specifically to a target sequence under optimum hybridization conditions as are known in the art. Primers and probes according to the present invention may have complete sequence complementarity with the target sequence, although probes differing from the target sequence and which retain the ability to hybridize to target sequences may be designed by conventional methods according to the invention.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

The polymerase chain reaction (PCR) is a technique for "amplifying" a particular piece of DNA. In order to perform PCR, at least a portion of the nucleotide sequence of the DNA molecule to be replicated must be known. In general, primers or short oligonucleotides are used that are complementary (e.g., substantially complementary or fully complementary) to the nucleotide sequence at the 3' end of each strand of the DNA to be amplified (known sequence). The DNA sample is heated to separate its strands and is mixed with the primers. The primers hybridize to their complementary sequences in the DNA sample. Synthesis begins (5' to 3' direction) using the original DNA strand as the template. The reaction mixture must contain all four deoxynucleotide triphosphates (dATP, dCTP, dGTP and dTTP) and a DNA polymerase. Polymerization continues until each newly-synthesized strand has proceeded far enough to contain the sequence recognized by the other primer. Once this occurs, two DNA molecules are created that are identical to the original molecule. These two molecules are heated to separate their strands and the process is repeated. Each cycle doubles the number of DNA molecules. Using automated equipment, each cycle of replication can be completed in less than 5 minutes. After 30 cycles, what began as a single molecule of DNA has been amplified into more than a billion copies ($2^{30}=1.02\times10^9$).

The oligonucleotides of an oligonucleotide primer pair are complementary to DNA sequences located on opposite DNA strands and flanking the region to be amplified. The annealed primers hybridize to the newly synthesized DNA strands. The first amplification cycle will result in two new DNA strands whose 5' end is fixed by the position of the oligonucleotide primer but whose 3' end is variable ('ragged' 3' ends). The two new strands can serve in turn as templates for synthesis of complementary strands of the desired length (the 5' ends are defined by the primer and the 3' ends are fixed because synthesis cannot proceed past the terminus of the opposing primer). After a few cycles, the desired fixed length product begins to predominate.

A quantitative polymerase chain reaction (qPCR), also referred to as real-time polymerase chain reaction, monitors the accumulation of a DNA product from a PCR reaction in real time. qPCR is a laboratory technique of molecular biology based on the polymerase chain reaction (PCR), which is used to amplify and simultaneously quantify a targeted DNA molecule. Even one copy of a specific sequence can be amplified and detected in PCR. The PCR reaction generates copies of a DNA template exponentially. This results in a quantitative relationship between the amount of starting target sequence and amount of PCR product accumulated at any particular cycle. Due to inhibitors of the polymerase reaction found with the template, reagent limitation or accumulation of pyrophosphate molecules, the PCR reaction eventually ceases to generate template at an exponential rate (i.e., the plateau phase), making the end point quantitation of PCR products unreliable. Therefore, duplicate reactions may generate variable amounts of PCR product. Only during the exponential phase of the PCR reaction is it possible to extrapolate back in order to determine the starting quantity of template sequence. The measurement of PCR products as they accumulate (i.e., real-time quantitative PCR) allows quantitation in the exponential phase of the reaction and therefore removes the variability associated with conventional PCR. In a real time PCR assay, a positive reaction is detected by accumulation of a fluorescent signal. For one or more specific sequences in a DNA sample, quantitative PCR enables both detection and quantification. The quantity can be either an absolute number of copies or a relative amount when normalized to DNA input or additional normalizing genes. Since the first documentation of real-time PCR, it has been used for an increasing and diverse number of applications including mRNA expression studies, DNA copy number measurements in genomic or viral DNAs, allelic discrimination assays, expression analysis of specific splice variants of genes and gene expression in paraffin-embedded tissues and laser captured micro-dissected cells.

As used herein, the phrase "Ct value" refers to "threshold cycle," which is defined as the "fractional cycle number at which the amount of amplified target reaches a fixed threshold." In some embodiments, it represents an intersection between an amplification curve and a threshold line. The amplification curve is typically in an "S" shape indicating the change of relative fluorescence of each reaction (Y-axis) at a given cycle (X-axis), which in some embodiments is recorded during PCR by a real-time PCR instrument. The threshold line is in some embodiments the level of detection at which a reaction reaches a fluorescence intensity above background. See Livak & Schmittgen (2001) 25 *Methods* 402-408. It is a relative measure of the concentration of the target in the PCR. Generally, good Ct values for quantitative assays such as qPCR are in some embodiments in the range of 10-40 for a given reference gene. Ct levels are inversely proportional to the amount of target nucleic acid in the sample (i.e. the lower the Ct level the greater the amount of detectable target nucleic acid in the sample). Additionally, good Ct values for quantitative assays such as qPCR show a linear response range with proportional dilutions of target gDNA.

In some embodiments, qPCR is performed under conditions wherein the Ct value can be collected in real-time for quantitative analysis. For example, in a typical qPCR experiment, DNA amplification is monitored at each cycle of PCR during the extension stage. The amount of fluorescence generally increases above the background when DNA is in the log linear phase of amplification. In some embodiments, the Ct value is collected at this time point.

As used herein, the term "cell" refers to any living cell. The cell may be a prokaryotic or eukaryotic cell. The cell may be isolated. The cell may or may not be capable of regenerating into an organism. The cell may be in the context of a tissue, callus, culture, organ, or part. In some embodiments, the cell may be a plant cell. A plant cell of the present invention can be in the form of an isolated single cell or can be a cultured cell or can be a part of a higher-organized unit such as, for example, a plant tissue or a plant organ. The plant cell may be derived from or part of an angiosperm or gymnosperm. In further embodiments, the plant cell may be a monocotyledonous plant cell, a dicotyledonous plant cell. The monocotyledonous plant cell may be, for example, a maize, rice, sorghum, sugarcane, barley, wheat, oat, turf grass, or ornamental grass cell. The dicotyledonous plant cell may be, for example, a tobacco, pepper, eggplant, sunflower, crucifer, flax, potato, cotton, soybean, sugar bee, or oilseed rape cell.

The term "plant part," as used herein, includes but is not limited to embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast.

The term "introducing" or "introduce" in the context of a cell, prokaryotic cell, bacterial cell, eukaryotic cell, plant cell, plant and/or plant part means contacting a nucleic acid molecule with the cell, eukaryotic cell, plant, plant part, and/or plant cell in such a manner that the nucleic acid molecule gains access to the interior of the cell, eukaryotic cell, plant cell and/or a cell of the plant and/or plant part. Where more than one nucleic acid molecule is to be introduced these nucleic acid molecules can be assembled as part of a single polynucleotide or nucleic acid construct, or as separate polynucleotide or nucleic acid constructs, and can be located on the same or different nucleic acid constructs. Accordingly, these polynucleotides can be introduced into plant cells in a single transformation event, in separate transformation events, or, e.g., as part of a breeding protocol.

As used herein, the terms "transformed" and "transgenic" refer to any cell, prokaryotic cell, eukaryotic cell, plant, plant cell, callus, plant tissue, or plant part that contains all or part of at least one recombinant (e.g., heterologous) polynucleotide. In some embodiments, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged, or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

The term "transformation" as used herein refers to the introduction of a heterologous nucleic acid into a cell. Transformation of a cell may be stable or transient. Thus, a transgenic cell, plant cell, plant and/or plant part of the invention can be stably transformed or transiently transformed.

Transformation can refer to the transfer of a nucleic acid molecule into the genome of a host cell, resulting in genetically stable inheritance. In some embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or any combination thereof.

Procedures for transforming plants are well known and routine in the art and are described throughout the literature. Non-limiting examples of methods for transformation of plants include transformation via bacterial-mediated nucleic acid delivery (e.g. via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Mild et al. ("Procedures for Introducing Foreign DNA into Plants" in Methods in *Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell Mol Biol Lett* 7:849-858 (2002)).

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. 1993, *Plant Cell* 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen and Willmitzer 1988, *Nucleic Acids Res* 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacteria or a bacteriophage, each containing one or more nucleic acids sought to be introduced) also can be propelled into plant tissue.

"Transient transformation" in the context of a polynucleotide means that a polynucleotide is introduced into the cell and does not integrate into the genome of the cell.

As used herein, "stably introducing," "stably introduced," "stable transformation" or "stably transformed" in the context of a polynucleotide introduced into a cell, means that the introduced polynucleotide is stably integrated into the genome of the cell, and thus the cell is stably transformed with the polynucleotide. As such, the integrated polynucleotide is capable of being inherited by the progeny thereof, more particularly, by the progeny of multiple successive generations. "Genome" as used herein includes the nuclear and/or plastid genome, and therefore includes integration of a polynucleotide into, for example, the chloroplast genome. Stable transformation as used herein can also refer to a polynucleotide that is maintained extrachromasomally, for example, as a minichromosome.

Transient transformation may be detected by, for example, an enzyme-linked immunosorbent assay (ELISA) or Western blot, which can detect the presence of a peptide or polypeptide encoded by one or more nucleic acid molecules introduced into an organism. Stable transformation of a cell can be detected by, for example, a Southern blot hybridization assay of genomic DNA of the cell with nucleic acid sequences which specifically hybridize with a nucleotide sequence of a nucleic acid molecule introduced into an organism (e.g., a plant). Stable transformation of a cell can be detected by, for example, a Northern blot hybridization assay of RNA of the cell with nucleic acid sequences which specifically hybridize with a nucleotide sequence of a nucleic acid molecule introduced into a plant or other organism. Stable transformation of a cell can also be detected by, e.g., a polymerase chain reaction (PCR) or other amplification reaction as are well known in the art, employing specific primer sequences that hybridize with target sequence(s) of a nucleic acid molecule, resulting in amplification of the target sequence(s), which can be detected according to standard methods. Transformation can also be detected by direct sequencing and/or hybridization protocols well known in the art.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (*Handbook of Plant Cell Cultures*, Vol. 1, MacMilan Publishing Co. New York (1983)); and Vasil I. R. (ed.) (*Cell Culture and Somatic Cell Genetics of Plants*, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

The terms "nucleotide sequence" "nucleic acid," "nucleic acid sequence," "nucleic acid molecule," "oligonucleotide" and "polynucleotide" are used interchangeably herein to refer to a heteropolymer of nucleotides and encompass both RNA and DNA, including cDNA, genomic DNA, mRNA, synthetic (e.g., chemically synthesized) DNA or RNA and chimeras of RNA and DNA. The term nucleic acid molecule refers to a chain of nucleotides without regard to length of the chain. The nucleotides contain a sugar, phosphate and a base which is either a purine or pyrimidine. A nucleic acid molecule can be double-stranded or single-stranded. Where single-stranded, the nucleic acid molecule can be a sense strand or an antisense strand. A nucleic acid molecule can be synthesized using oligonucleotide analogs or derivatives (e.g., inosine or phosphorothioate nucleotides). Such oligonucleotides can be used, for example, to prepare nucleic acid molecules that have altered base-pairing abilities or increased resistance to nucleases. Nucleic acid sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25.

A "nucleic acid fragment" is a fraction of a given nucleic acid molecule. An "RNA fragment" is a fraction of a given RNA molecule. A "DNA fragment" is a fraction of a given DNA molecule. A "nucleic acid segment" is a fraction of a given nucleic acid molecule and is not isolated from the molecule. An "RNA segment" is a fraction of a given RNA molecule and is not isolated from the molecule. A "DNA segment" is a fraction of a given DNA molecule and is not isolated from the molecule. Segments of polynucleotides can be any length, for example, at least 5, 10, 15, 20, 25, 30, 40, 50, 75, 100, 150, 200, 300 or 500 or more nucleotides in length. A segment or portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

The term "derived from" in the context of a molecule refers to a molecule isolated or made using a parent molecule or information from that parent molecule. For example, a Cas9 single mutant nickase and a Cas9 double mutant null-nuclease are derived from a wild-type Cas9 protein.

In higher plants, deoxyribonucleic acid (DNA) is the genetic material while ribonucleic acid (RNA) is involved in the transfer of information contained within DNA into proteins. A "genome" is the entire body of genetic material contained in each cell of an organism. Unless otherwise indicated, a particular nucleic acid sequence of this invention also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98 (1994)). The term nucleic acid molecule is used interchangeably with gene, cDNA, and mRNA encoded by a gene.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," in the context of two nucleic acid molecules, nucleotide sequences or protein sequences, refers to two or more sequences or subsequences that have at least about 70%, least about 75%, at least about 80%, least about 85%, at least about 90%, at least about 95%, at least about 96%, at least about 97%, at least about 98%, or at least about 99% nucleotide or amino acid residue identity, when compared and aligned for maximum correspondence, as measured using one of the following sequence comparison algorithms or by visual inspection. In some embodiments of the invention, the substantial identity exists over a region of the sequences that is at least about 50 residues to about 150 residues in length. Thus, in some embodiments of this invention, the substantial identity exists over a region of the sequences that is at least about 50, about 60, about 70, about 80, about 90, about 100, about 110, about 120, about 130, about 140, about 150, or more residues in length. In some particular embodiments, the sequences are substantially identical over at least about 150 residues. In a further embodiment, the sequences are substantially identical over the entire length of the coding regions. Furthermore, in representative embodiments, substantially identical nucleotide or protein sequences perform substantially the same function (e.g., guiding to a particular genomic target, endonuclease cleavage of a particular genomic target site).

For sequence comparison, typically one sequence acts as a reference sequence to which test sequences are compared.

When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially identical when the two sequences hybridize to each other under stringent conditions. In some representative embodiments, two nucleotide sequences considered to be substantially identical hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology—Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the present invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1×SSC, 0.1% SDS at 65° C.

An "isolated" nucleic acid molecule or nucleotide sequence or an "isolated" polypeptide is a nucleic acid molecule, nucleotide sequence or polypeptide that, by the hand of man, exists apart from its native environment and/or has a function that is different, modified, modulated and/or altered as compared to its function in its native environment and is therefore not a product of nature. An isolated nucleic acid molecule or isolated polypeptide may exist in a purified form or may exist in a non-native environment such as, for example, a recombinant host cell. Thus, for example, with respect to polynucleotides, the term isolated means that it is separated from the chromosome and/or cell in which it naturally occurs. A polynucleotide is also isolated if it is separated from the chromosome and/or cell in which it naturally occurs and is then inserted into a genetic context, a chromosome, a chromosome location, and/or a cell in which it does not naturally occur. The recombinant nucleic acid molecules and nucleotide sequences of the invention can be considered to be "isolated" as defined above.

Thus, an "isolated nucleic acid molecule" or "isolated nucleotide sequence" is a nucleic acid molecule or nucleotide sequence that is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant nucleic acid that is part of a hybrid nucleic acid molecule encoding an additional polypeptide or peptide sequence. An "isolated nucleic acid molecule" or "isolated nucleotide sequence" can also include a nucleotide sequence derived from and inserted into the same natural, original cell type, but which is present in a non-natural state, e.g., present in a different copy number, and/or under the control of different regulatory sequences than that found in the native state of the nucleic acid molecule.

The term "isolated" can further refer to a nucleic acid molecule, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid molecule, nucleotide sequence or polypeptide that is not naturally occurring as a fragment and would not be found as such in the natural state. "Isolated" does not necessarily mean that the preparation is technically pure (homogeneous), but it is sufficiently pure to provide the polypeptide or nucleic acid in a form in which it can be used for the intended purpose.

In representative embodiments of the invention, an "isolated" nucleic acid molecule, nucleotide sequence, and/or polypeptide is at least about 5%, 10%, 15%, 20%, 25%, 30%, 40%, 50%, 60%, 70%, 75%, 80%, 85%, 90%, 95%, 97%, 98%, 99% pure (w/w) or more. In other embodiments, an "isolated" nucleic acid, nucleotide sequence, and/or polypeptide indicates that at least about a 5-fold, 10-fold, 25-fold, 100-fold, 1000-fold, 10,000-fold, 100,000-fold or more enrichment of the nucleic acid (w/w) is achieved as compared with the starting material.

"Wild-type" nucleotide sequence or amino acid sequence refers to a naturally occurring ("native") or endogenous nucleotide sequence or amino acid sequence. Thus, for example, a "wild-type mRNA" is an mRNA that is naturally occurring in or endogenous to the organism. A "homologous" nucleotide sequence is a nucleotide sequence naturally associated with a host cell into which it is introduced.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Promoter" refers to a nucleotide sequence, usually upstream (5') to its coding sequence, which controls the expression of the coding sequence by providing the recognition for RNA polymerase and other factors required for proper transcription. "Promoter regulatory sequences" consist of proximal and more distal upstream elements. Promoter regulatory sequences influence the transcription, RNA processing or stability, or translation of the associated coding sequence. Regulatory sequences include enhancers, promoters, untranslated leader sequences, introns, and polyadenylation signal sequences. They include natural and synthetic sequences as well as sequences that may be a combination of synthetic and natural sequences. An "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. The meaning of the term "promoter" includes "promoter regulatory sequences."

"Primary transformant" and "TO generation" refer to transgenic plants that are of the same genetic generation as the tissue that was initially transformed (i.e., not having gone through meiosis and fertilization since transformation). "Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

A "transgene" refers to a nucleic acid molecule that has been introduced into the genome by transformation and is stably maintained. A transgene may comprise at least one expression cassette, typically comprises at least two expression cassettes, and may comprise ten or more expression cassettes. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but one that is introduced into the organism by gene transfer.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. For purposes of the present invention, the definition of the term "intron" includes modifications to the nucleotide sequence of an intron derived from a target gene, provided the modified intron does not significantly reduce the activity of its associated 5' regulatory sequence.

"Exon" refers to a section of DNA which carries the coding sequence for a protein or part of it. Exons are separated by intervening, non-coding sequences (introns). For purposes of the present invention, the definition of the term "exon" includes modifications to the nucleotide sequence of an exon derived from a target gene, provided the modified exon does not significantly reduce the activity of its associated 5' regulatory sequence.

The term "cleavage" or "cleaving" refers to breaking of the covalent phosphodiester linkage in the ribosylphosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends. A "nuclease cleavage site" or "genomic nuclease cleavage site" is a region of nucleotides that comprise a nuclease cleavage sequence that is recognized by a specific nuclease, which acts to cleave the nucleotide sequence of the genomic DNA in one or both strands. Such cleavage by the nuclease enzyme initiates DNA repair mechanisms within the cell, which establishes an environment for homologous recombination to occur.

A "donor molecule" or "donor sequence" is a nucleotide polymer or oligomer intended for insertion at a target polynucleotide, typically a target genomic site. The donor sequence may be one or more transgenes, expression cassettes, or nucleotide sequences of interest. A donor molecule may be a donor DNA molecule, either single stranded, partially double-stranded, or double-stranded. The donor polynucleotide may be a natural or a modified polynucleotide, a RNA-DNA chimera, or a DNA fragment, either single- or at least partially double-stranded, or a fully double-stranded DNA molecule, or a PGR amplified ssDNA or at least partially dsDNA fragment. In some embodiments, the donor DNA molecule is part of a circularized DNA molecule. A fully double-stranded donor DNA is advantageous since it might provide an increased stability, since dsDNA fragments are generally more resistant than ssDNA to nuclease degradation. In some embodiments, the donor polynucleotide molecule can comprise at least about 100, 150, 200, 250, 300, 250, 400, 450, 500, 600, 700, 800, 900, 1000, 1500, 2000, 2500, 3000, 3500, 4000, 4500, 5000, 7500, 10000, 15,000 or 20,000 nucleotides, including any value within this range not explicitly recited herein. In some embodiments, the donor DNA molecule comprises heterologous nucleic acid sequence. In some embodiments, the donor DNA molecule comprises at least one expression cassette. In some embodiments, the donor DNA molecule may comprise a transgene, which comprises at least one expression cassette. In some embodiments, the donor DNA molecule comprises an allelic modification of a gene which is native to the target genome. The allelic modification may comprise at least one nucleotide insertion, at least one nucleotide deletion, and/or at least one nucleotide substitution. In some embodiments, the allelic modification may comprise an INDEL. In some embodiments, the donor DNA molecule comprises homologous arms to the target genomic site. In some embodiments, the donor DNA molecule comprises at least 100 contiguous nucleotides at least 90% identical to a genomic nucleic acid sequence, and optionally may further comprise a heterologous nucleic acid sequence such as a transgene.

As used herein, a "target site," "target sequence", "target genomic site" "targeted genomic site" or "target" refers to a region of contiguous nucleic acids in the genome that is the selected or preferred site for insertion of a nucleotide sequence, for example a donor DNA molecule. A target polynucleotide may be single stranded or double-stranded, and, in certain embodiments, is at least partially double-stranded DNA. In some embodiments, a target site can comprise a nuclease cleavage site, also referred to as a genomic nuclease cleavage site. A nonlimiting example of a target site of this invention is the chromosome interval on chromosome 1 defined by and including base pair (bp) position 38,860,000 to base pair (bp) position 39,105,000 as defined by Maize B73 RefGen_V2 available in the Maize Genome Database (US Patent Publication US2017/0016010A1 hereby incorporated within). Another example of a target site is a region of a gene targeted for mutagenesis.

As used herein, the terms "proximal" or "proximal to" with regard to one or more nucleotide sequences of this invention means immediately next to (e.g., with no intervening sequence) or separated by from about 1 base to about 500 bases (e.g., 1, 2, 3, 4, 5, 6, 7, 8, 9, 10, 15, 20, 30, 40, 50, 100, 200, 250, 300, 350, 400, 450, or 500 bases), including any values included within this range but not explicitly recited herein.

As used herein, the term "bait RNA" refers to an RNA molecule or portion thereof that includes at least 8 nucleotides that are at least 70% complementary to at least 8 nucleotides of the donor polynucleotide. In some embodiments, the bait RNA is a segment of the guide RNA. In some embodiments, the bait RNA is a segment of a chimeric guide RNA, which may also be referred to as a chimeric RNA. In some embodiments, the bait RNA is linked to the 5' and/or 3' end of the tracrRNA. In some embodiments, the bait RNA is linked to the 5' and/or 3' end of the crRNA. In some embodiments, the bait RNA is linked to the tracrRNA and the crRNA is a separate RNA molecule, as in a dual-guide RNA. In some embodiments, the bait RNA is linked to the crRNA and the tracrRNA is a separate RNA molecule, as in a dual-guide RNA. In some embodiments, the bait RNA is linked to the crRNA and there is no tracrRNA, as in a CRISPR-Cas system where the nuclease is Cpf1. In some embodiments, the bait RNA may be substantially complementary to a fragment of the donor DNA molecule. The bait RNA may be located at the 5' end or the 3'end of the guide RNA molecule, or between the crRNA and tracrRNA segments of the guide RNA.

As used herein, the term "guide RNA" or "gRNA" generally refers to an RNA molecule (or a group of RNA molecules collectively) that can bind to a CRISPR system effector, such as a Cas or a Cpf1 protein, and aid in targeting the Cas or Cpf1 protein to a specific location within a target polynucleotide (e.g., a DNA). A guide RNA of the invention can be an engineered, single RNA molecule (sgRNA), where for example the sgRNA comprises a crRNA segment and optionally a tracrRNA segment. A guide RNA of the invention can also be a dual-guide system, where the crRNA and tracrRNA molecules are physically distinct molecules which then interact to form a duplex for recruitment of a CRISPR system effector, such as Cas9, and for targeting of that protein to the target polynucleotide.

As used herein, the term "crRNA" or "crRNA segment" refers to an RNA molecule or to a portion of an RNA molecule that includes a polynucleotide targeting guide sequence, a stem sequence involved in protein-binding, and, optionally, a 3'-overhang sequence. The polynucleotide targeting guide sequence is a nucleic acid sequence that is complementary to a sequence in a target DNA. This polynucleotide targeting guide sequence is also referred to as the "protospacer". In other words, the polynucleotide targeting guide sequence of a crRNA molecule interacts with a target DNA in a sequence-specific manner via hybridization (i.e., base pairing). As such, the nucleotide sequence of the polynucleotide targeting guide sequence of the crRNA molecule may vary and determines the location within the target DNA that the guide RNA and the target DNA will interact.

The polynucleotide targeting guide sequence of a crRNA molecule can be modified (e.g., by genetic engineering) to hybridize to any desired sequence within a target DNA. The polynucleotide targeting guide sequence of a crRNA molecule of the invention can have a length from about 12 nucleotides to about 100 nucleotides. For example, the polynucleotide targeting guide sequence of a crRNA can have a length of from about 12 nucleotides (nt) to about 80 nt, from about 12 nt to about 50 nt, from about 12 nt to about 40 nt, from about 12 nt to about 30 nt, from about 12 nt to about 25 nt, from about 12 nt to about 20 nt, or from about 12 nt to about 19 nt. For example, the polynucleotide targeting guide sequence of a crRNA can have a length of from about 17 nt to about 27 nts. For example, the polynucleotide targeting guide sequence of a crRNA can have a length of from about 19 nt to about 20 nt, from about 19 nt to about 25 nt, from about 19 nt to about 30 nt, from about 19 nt to about 35 nt, from about 19 nt to about 40 nt, from about 19 nt to about 45 nt, from about 19 nt to about 50 nt, from about 19 nt to about 60 nt, from about 19 nt to about 70 nt, from about 19 nt to about 80 nt, from about 19 nt to about 90 nt, from about 19 nt to about 100 nt, from about 20 nt to about 25 nt, from about 20 nt to about 30 nt, from about 20 nt to about 35 nt, from about 20 nt to about 40 nt, from about 20 nt to about 45 nt, from about 20 nt to about 50 nt, from about 20 nt to about 60 nt, from about 20 nt to about 70 nt, from about 20 nt to about 80 nt, from about 20 nt to about 90 nt, or from about 20 nt to about 100 nt. The nucleotide sequence of the polynucleotide targeting guide sequence of a crRNA can have a length at least about 12 nt. In some embodiments, the polynucleotide targeting guide sequence of a crRNA is 20 nucleotides in length. In some embodiments, the polynucleotide targeting guide sequence of a crRNA is 19 nucleotides in length.

The present invention also provides a guide RNA comprising an engineered crRNA, wherein the crRNA comprises a bait RNA segment capable of hybridizing to a genomic target sequence. This engineered crRNA maybe a physically distinct molecule, as in a dual-guide system.

As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The present invention also provides a guide RNA comprising an engineered tracrRNA, wherein the tracrRNA further comprises a bait RNA segment that is capable of binding to a donor DNA molecule. The engineered tracrRNA may be a physically distinct molecule, as in a dual-guide system, or may be a segment of a sgRNA molecule.

In some embodiments, the guide RNA, either as a sgRNA or as two or more RNA molecules, does not contain a tracrRNA, as it is known in the art that some CRISPR-associated nucleases, such as Cpf1 (also known as Cas12a), do not require a tracrRNA for its RNA-mediated endonuclease activity (Qi et al., 2013, Cell, 152: 1173-1183; Zetsche et al., 2015, Cell 163: 759-771). Such a guide RNA of the invention may comprise a crRNA with the bait RNA operably linked at the 5' or 3' end of the crRNA. Cpf1 also has RNase activity on its cognate pre-crRNA (Fonfara et al., 2016, Nature, doi.org/10.1038/nature17945). A guide RNA of the invention may comprise multiple crRNAs which the Cpf1 possesses to mature crRNAs. In some embodiments, each of these crRNAs is operably linked to a bait RNA. In other embodiments, at least one of these crRNAs is operably linked to a bait RNA. The bait RNA may be specific to a sequence of interest (SOI), as shown in FIG. 1 and as described in the Examples herein, or it may be a "universal" bait, which has a corresponding "universal" prey sequence on the donor DNA molecule, as shown in FIG. 2 and as described in the Examples herein.

As used herein, the term "chimeric RNA" refers to an RNA molecule or more than one RNA molecule comprising a guide RNA and a bait RNA. In some embodiments, the chimeric RNA is a single guide RNA molecule which comprises a bait RNA. In some embodiments, the bait RNA is operably linked to the chimeric RNA at the 5' end of the guide RNA. In other embodiments, the bait RNA is operably linked to the chimeric RNA at the 3' end of the guide RNA.

In some embodiments, the chimeric RNA refers to an RNA molecule comprising an crRNA and a bait RNA molecule. In other embodiments, the chimeric RNA refers to more than one RNA molecule, as in a dual-guide RNA system, where the chimeric RNA refers to a crRNA and a tracrRNA, wherein either the crRNA and/or the tracrRNA may be modified to comprise a bait RNA. In some embodiments, a bait RNA is operably linked to the crRNA at its 5' or 3' end. In some embodiments, a bait RNA is operably linked to the tracrRNA at its 5' or 3' end.

In some embodiments, the chimeric RNA of the invention comprises a guide RNA which comprises a nucleic acid sequence which is a binding site for a site-directed modifying polypeptide. In some embodiments, the chimeric RNA comprises a guide RNA which further comprises a tracrRNA, wherein the tracrRNA interacts with the guide RNA (either intramolecularly, as for a single guide RNA molecule, or intermolecularly, as in a dual-guide RNA system), to create an RNA duplex that is a binding site for a site-directed modifying polypeptide.

In some embodiments, the chimeric RNA of the invention comprises a bait RNA that is at least 8 contiguous nucleic acids, or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 contiguous nucleic acids, including any value within this range not explicitly recited herein. The nucleic acid sequence of the bait RNA is at least 70%, 75%, 80%, 85%, 86%, 87%, 88%, 89%, 90%, 91%, 92%, 93%, 94%, 95%, 96%, 97%, 98%, or at least 99% or 100% identical to at least 8 contiguous nucleic acids, or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 nucleic acids, including any value within this range not explicitly recited herein, of a donor DNA molecule and is capable of hybridizing to the donor DNA molecule. In some embodiments, the bait RNA may be substantially complementary to a fragment of the donor DNA molecule. The donor DNA molecule is intended for integration into the genome of a plant cell. In embodiments, the hybridization of the bait RNA with the donor DNA molecule forms an RNA:DNA heteroduplex. In some embodiments, the hybridization may form a three-stranded nucleic acid complex, comprising complementary strands of DNA and the bait RNA. In other embodiments, the hybridization may form a combination of RNA:DNA duplex and three-stranded nucleic acid complex. The complementary region of the donor DNA molecule to which the bait RNA hybridizes may be referred to as the "prey sequence" or the "donor prey sequence".

The present invention provides a chimeric RNA for targeted genomic modification of a cell, wherein the chimeric RNA comprises: (a) a crRNA comprising a nucleic acid sequence encoding a guide sequence capable of hybridizing to a target nucleic acid molecule encoding a target sequence; (b) a bait RNA comprising at least 8 contiguous nucleic acids, wherein the nucleic acid sequence of the bait RNA is at least 70% complementary to at least 8 contiguous nucleic acids of a donor DNA molecule and is capable of hybridizing to the donor DNA molecule, wherein the donor DNA molecule is intended for integration into the genome of a plant cell.

The present invention also provides a nucleic acid molecule comprising a nucleic acid sequence encoding a guide RNA of the invention. The nucleic acid molecule may be a DNA or an RNA molecule. In some embodiments, the nucleic acid molecule is circularized. In other embodiments, the nucleic acid molecule is linear. In some embodiments, the nucleic acid molecule is single stranded, partially double-stranded, or double-stranded. In some embodiments, the nucleic acid molecule is complexed with at least one polypeptide. The polypeptide may have a nucleic acid recognition or nucleic acid binding domain. In some embodiments, the polypeptide is a shuttle for mediating delivery of, for example, a chimeric RNA of the invention, a nuclease, and optionally a donor molecule. In some embodiments, the polypeptide is a Feldan Shuttle (U.S. Patent Publication No. 20160298078, herein incorporated by reference). The nucleic acid molecule may comprise an expression cassette capable of driving the expression of the chimeric RNA. The nucleic acid molecule may further comprise additional expression cassettes, capable of expressing, for example, a nuclease such as a CRISPR-associated nuclease. The present invention also provides an expression cassette comprising a nucleic acid sequence encoding a chimeric RNA of the invention.

A "site-directed modifying polypeptide" modifies the target DNA (e.g., cleavage or methylation of target DNA) and/or a polypeptide associated with target DNA (e.g., methylation or acetylation of a histone tail). A site-directed modifying polypeptide is also referred to herein as a "site-directed polypeptide" or an "RNA binding site-directed modifying polypeptide." The site-directed modifying polypeptide interacts with the guide RNA, which is either a single RNA molecule or a RNA duplex of at least two RNA molecules, and is guided to a DNA sequence (e.g. a chromosomal sequence or an extrachromosomal sequence, e.g. an episomal sequence, a minicircle sequence, a mitochondrial sequence, a chloroplast sequence, etc.) by virtue of its association with the guide RNA.

In some cases, the site-directed modifying polypeptide is a naturally-occurring modifying polypeptide. In other cases, the site-directed modifying polypeptide is not a naturally-occurring polypeptide (e.g., a chimeric polypeptide or a naturally-occurring polypeptide that is modified, e.g., mutation, deletion, insertion). Exemplary naturally-occurring site-directed modifying polypeptides are known in the art (see for example, Makarova et al., 2017, Cell 168: 328-328.e1, and Shmakov et al., 2017, Nat Rev Microbiol 15(3): 169-182, both herein incorporated by reference). These naturally occurring polypeptides bind a DNA-targeting RNA, are thereby directed to a specific sequence within a target DNA, and cleave the target DNA to generate a double strand break.

A site-directed modifying polypeptide comprises two portions, an RNA-binding portion and an activity portion. In some embodiments, the site-directed modifying polypeptide comprises: (i) an RNA-binding portion that interacts with a DNA-targeting RNA, wherein the DNA-targeting RNA comprises a nucleotide sequence that is complementary to a sequence in a target DNA; and (ii) an activity portion that exhibits site-directed enzymatic activity (e.g., activity for DNA methylation, activity for DNA cleavage, activity for histone acetylation, activity for histone methylation, etc.), wherein the site of enzymatic activity is determined by the DNA-targeting RNA. In other embodiments, a site-directed modifying polypeptide comprises: (i) an RNA-binding portion that interacts with a DNA-targeting RNA, wherein the DNA-targeting RNA comprises a nucleotide sequence that is complementary to a sequence in a target DNA; and (ii) an activity portion that modulates transcription within the target DNA (e.g., to increase or decrease transcription), wherein the site of modulated transcription within the target DNA is determined by the DNA-targeting RNA.

In some cases, the site-directed modifying polypeptide has enzymatic activity that modifies target DNA (e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity). In other cases, the site-directed modifying polypeptide has enzymatic activity that modifies a polypeptide (e.g., a histone) associated with target DNA (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

In some cases, different site-directed modifying polypeptides, for example different Cas9 proteins (i.e., Cas9 proteins from various species) may be advantageous to use in the various provided methods of the invention to capitalize on various enzymatic characteristics of the different Cas9 proteins (e.g., for different PAM sequence preferences; for increased or decreased enzymatic activity;

for an increased or decreased level of cellular toxicity; to change the balance between NHEJ, homology-directed repair, single strand breaks, double strand breaks, etc.). Cas9 proteins from various species (for example, those disclosed in Shmakov et al., 2017, or polypeptides derived therefrom) may require different PAM sequences in the target DNA. Thus, for a particular Cas9 enzyme of choice, the PAM sequence requirement may be different than the 5'-N GG-3' sequence (where N is either a A, T, C, or G) known to be required for Cas9 activity. Many Cas9 orthologues from a wide variety of species have been identified herein and the proteins share only a few identical amino acids. All identified Cas9 orthologs have the same domain architecture with a central HNH endonuclease domain and a split RuvC/RNaseH domain. Cas9 proteins share 4 key motifs with a conserved architecture; Motifs 1, 2, and 4 are RuvC like motifs, while motif 3 is an HNH-motif.

The site-directed modifying polypeptide may also be a chimeric and modified Cas9 nuclease. For example, it may be a modified Cas9 "base editor". Base editing enables direct, irreversible conversion of one target DNA base into another in a programmable manner, without requiring DNA cleavage or a donor DNA molecule. For example, Komor et al (2016, Nature, 533: 420-424), teach a Cas9-cytidine deaminase fusion, where the Cas9 has also been engineered to be inactivated and not induce double-stranded DNA breaks. Additionally, Gaudelli et al (2017, Nature, doi: 10.1038/nature24644) teach a catalytically impaired Cas9 fused to a tRNA adenosine deaminase, which can mediate conversion of an A/T to G/C in a target DNA sequence. Another class of engineered Cas9 nucleases which may act as a site-directed modifying polypeptide in the methods and compositions of the invention are variants which can recognize a broad range of PAM sequences, including NG, GAA, and GAT (Hu et al., 2018, Nature, doi:10.1038/nature26155).

Any Cas9 protein, including those naturally occurring and/or those mutated or modified from naturally occurring Cas9 proteins, can be used as a site-directed modifying polypeptide in the methods and compositions of the present invention. Catalytically active Cas9 nucleases cleave target DNA to produce double strand breaks. These breaks are then repaired by the cell in one of two ways: non-homologous end joining, and homology-directed repair.

In non-homologous end joining (NHEJ), the double-strand breaks are repaired by direct ligation of the break ends to one another. As such, no new nucleic acid material is inserted into the site, although some nucleic acid material may be lost, resulting in a deletion. In homology-directed repair, a donor DNA molecule with homology to the cleaved target DNA sequence is used as a template for repair of the cleaved target DNA sequence, resulting in the transfer of genetic information from the donor polynucleotide to the target DNA. As such, new nucleic acid material may be inserted/copied into the site. In some cases, a target DNA is contacted with a donor molecule, for example a donor DNA molecule. In some cases, a donor DNA molecule is introduced into a cell. In some cases, at least a segment of a donor DNA molecule integrates into the genome of the cell.

The modifications of the target DNA due to NHEJ and/or homology-directed repair lead to, for example, gene correction, gene replacement, gene tagging, transgene insertion, nucleotide deletion, gene disruption, gene mutation, etc. Accordingly, cleavage of DNA by a site-directed modifying polypeptide may be used to delete nucleic acid material from a target DNA sequence (e.g., to disrupt a gene that makes cells susceptible to infection (e.g. the CCR5 or CXCR4 gene, which makes T cells susceptible to HIV infection), to remove disease-causing trinucleotide repeat sequences in neurons, to create gene knockouts and mutations as disease models in research, etc.) by cleaving the target DNA sequence and allowing the cell to repair the sequence in the absence of an exogenously provided donor polynucleotide. Thus, the subject methods can be used to knock out a gene (resulting in complete lack of transcription or altered transcription) or to knock in genetic material into a locus of choice in the target DNA. Alternatively, if a DNA-targeting RNA duplex and a site-directed modifying polypeptide are co-administered to cells with a donor molecule that includes at least a segment with homology to the target DNA sequence, the subject methods may be used to add, i.e. insert or replace, nucleic acid material to a target DNA sequence (e.g. to "knock in" a nucleic acid that encodes for a protein, an siRNA, an miRNA, etc.), to add a tag (e.g., 6xHis, a fluorescent protein (e.g., a green fluorescent protein; a yellow fluorescent protein, etc.), hemagglutinin (HA), FLAG, etc.), to add a regulatory sequence to a gene (e.g. promoter, polyadenylation signal, internal ribosome entry sequence (IRES), 2A peptide, start codon, stop codon, splice signal, localization signal, etc.), to modify a nucleic acid sequence (e.g., introduce a mutation), and the like. As such, a complex comprising a DNA-targeting RNA duplex and a site-directed modifying polypeptide is useful in any in vitro or in vivo application in which it is desirable to modify DNA in a site-specific, i.e. "targeted", way, for example gene knock-out, gene knock-in, gene editing, gene tagging, etc., as used in, for example, gene therapy, e.g. to treat a disease or as an antiviral, antipathogenic, or anticancer therapeutic, the production of genetically modified organisms in agriculture, the large scale production of proteins by cells for therapeutic, diagnostic, or research purposes, the induction of iPS cells, biological research, the targeting of genes of pathogens for deletion or replacement, etc.

The term "CRISPR-associated protein", "Cas protein", "CRISPR-associated nuclease" or "Cas nuclease" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the Cas mutant or Cas variant substantially retains the nuclease activity of the Cas protein, such as a Cas9 variant described herein which is operably linked to a nuclear localization signal (NLS) derived from a plant. In certain embodiments, the Cas nuclease is mutated such that one or both nuclease domains are inactive, such as, for example, a catalytically dead Cas9 referred to as dCas9, which is still able to target to a specific genomic location but has no endonuclease activity (Qi et al., 2013, Cell, 152: 1173-1183, hereby incorporated within). In some embodiments, the Cas nuclease is mutated so that it lacks some or all of the nuclease activity of its wild-type counterpart. The Cas protein may be Cas9, Cpf1 (Zetsche et al., 2015, Cell, 163: 759-771, hereby incorporated within) or any another CRISPR-associated nuclease.

The present invention provides a method of integrating a transgene into a target genomic site in the genome of a cell, comprising introducing into the cell: a) a first nucleic acid molecule comprising a donor DNA molecule, which comprises at least 10 contiguous nucleotides at least 70% identical to a genomic nucleic acid sequence, and further comprises a transgene, and b) a second nucleic acid molecule comprising a nucleotide sequence encoding a nuclease for site-directed cleavage at a target genomic site proximal to the genomic nucleic acid sequence of part a), and further comprising at least one nucleic acid sequence encoding the chimeric RNA of the invention, wherein the bait RNA encodes at least 8 contiguous nucleotides that are at least 70% complementary to a region of the transgene. These nucleic acid molecules are introduced into the cell under conditions wherein expression of the second nucleic acid molecule can occur to produce the nuclease and the nuclease can cleave the nucleotide sequence at the target genomic site, whereby the transgene is integrated at the target genomic site in the genome of the cell.

The present invention also provides a method of integrating a transgene into a target genomic site in the genome of a cell, comprising providing to the cell: a) a first nucleic acid molecule comprising a donor DNA molecule comprising a transgene, and further comprising at least 10 contiguous nucleic acids which are at least 70% identical to a genomic nucleic acid sequence, b) a second nucleic acid comprising at least one nucleic acid sequence comprising a chimeric RNA of the invention, wherein the target nucleic acid sequence is a target genomic site of the cell, and c) a nuclease capable of site-directed cleavage at the target genomic site proximal to the genomic nucleic acid sequence of part a) under conditions wherein the nuclease can cleave the targeted genomic nucleotide sequence at the target genomic site, whereby the transgene is integrated at the target genomic site in the genome of the cell. The second nucleic acid comprising the chimeric RNA of the invention may be pre-bound to the nuclease. Because the chimeric RNA comprises the bait RNA which is at least partially complementary to the donor DNA molecule, it is possible that the nuclease, chimeric RNA, and donor DNA are provided to the cell as a complex. This complex may be further complexed with other polypeptides, for example a Feldan shuttle.

The present invention also provides a method of integration of a transgene into a target genomic site of a cell, comprising providing to the cell: a) a first nucleic acid molecule comprising a donor DNA molecule comprising a transgene, and further comprising at least 10 contiguous nucleic acids which are at least 80% identical to a genomic nucleic acid sequence; b) a second nucleic acid comprising at least one nucleic acid sequence comprising a chimeric RNA the invention, wherein the target nucleic acid sequence is a target genomic site of the cell; c) a nuclease capable of site-directed cleavage at the target genomic site proximal to the genomic nucleic acid sequence of part a), and d) a RNA binding protein capable of binding to the chimeric RNA of part b), under conditions wherein the nuclease can cleave the targeted genomic nucleotide sequence at the target genomic site, whereby the transgene is integrated at the target genomic site in the genome of the cell. In some embodiments, the nuclease may be a site specific nuclease, such a meganuclease, a zinc finger nuclease, a TALEN, for a CRISPR-associated nuclease. In some embodiments, the RNA binding protein is a dCas9 ("dead" Cas9) or dCpf1 ("dead" Cpf1), wherein the nuclease activity of the RNA binding protein is inactivated.

In some embodiments of the methods of the invention of integrating a transgene into a target genomic site in the genome of a cell, the cell is a eukaryotic cell. In some embodiments, the cell is a plant cell. In some embodiments, the cell is a coniferous cell. In other embodiments, the cell is a monocotyledonous or dicotyledonous plant cell. In further embodiments, the cell is a maize, rice, sorghum, sugarcane, barley, wheat, oat, turf grass, ornamental grass, tobacco, tomato, pepper, eggplant, sunflower, crucifer, flax, potato, cotton, soybean, sugar beet, or oilseed rape cell. In some embodiments, the first and/or second nucleic acid molecules may be introduced into the cell by biolistic nucleic acid delivery, via an *Agrobacterium*, by co-transformation, and/or with a T-DNA vector in any combination and/or order. In some embodiments, the first and second nucleic acid molecules are present on a single nucleic acid construct. In some embodiments, the first and second nucleic acid molecules are present on separate nucleic acid constructs. In other embodiments, the first and/or the second nucleic acid molecules are transiently expressed in the cell. In some embodiments, the first and/or the second nucleic acid molecules are stably transformed into a cell.

In some embodiments of the methods of the invention of integrating a transgene into a target genomic site in the genome of a cell, the chimeric RNA comprises a guide RNA and a bait RNA that is at least 8 contiguous nucleic acids and is at least 70% complementary to the transgene of the donor molecule. In other embodiments, the chimeric RNA comprises a guide RNA and a bait RNA that is at least 8 contiguous nucleic acids and is at least 70% complementary to the genomic nucleic acid sequence of part a) of the methods of the invention described above. In other embodiments, the chimeric RNA comprises a guide RNA and a bait RNA that is at least 70% complementary to at least 8 contiguous nucleic acids to a fragment of the donor DNA molecule, wherein the fragment is neither the transgene nor the genomic nucleic acid sequence of part a) of the methods of the invention described above.

In some embodiments, the invention provides the methods described above where the first nucleic acid molecule comprising a donor DNA molecule may comprise at least 10 contiguous nucleic acids, wherein the nucleic acid molecule is at least 70% identical to a genomic nucleic acid sequence, such that these contiguous nucleotides are sufficient for homologous recombination of the donor DNA molecule, which further comprises a transgene, into the genome of the cell at the targeted genomic site following targeted nuclease cleavage. In other embodiments, a donor DNA molecule may comprise at least 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, or at least 1,000 contiguous nucleic acids, wherein said nucleic acid molecule is at least 70%, 75%, 80%, 85%, 86%, 87%, 88%, 89%, 90%, 91%, 92%, 93%, 94%, 95%, 96%, 97%, 98%, or at least 99% or 100% identical to a genomic nucleic acid sequence, and further comprise a transgene. In some embodiments, the donor DNA molecule may be substantially complementary to a genomic nucleic acid sequence. In some embodiments, the donor DNA molecule is single stranded. In other embodiments, the donor DNA molecule is at least partially double stranded.

In some embodiments, the invention provides the methods described above where the second nucleic acid molecule encodes a site-directed modifying polypeptide. In further embodiments, the site-directed modifying polypeptide is a nuclease that is an endonuclease, for example a meganuclease, a zinc finger nuclease, or a TALEN. In some embodiments, the nuclease is an RNA-guided endonuclease. In further embodiments, the nuclease is a CRISPR-associated nuclease, for example Cas9 or Cpf1.

In some embodiments, the invention provides the method described above where the second nucleic acid molecule further comprises a chimeric RNA which comprises a guide RNA and a bait RNA that is at least 8 or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 contiguous nucleic acids, including any value within this range not explicitly recited herein. The nucleic acid sequence of the bait RNA may be at least 70%, 75%, 80%, 85%, 86%, 87%, 88%, 89%, 90%, 91%, 92%, 93%, 94%, 95%, 96%, 97%, 98%, or at least 99% or 100% identical to at least 8 contiguous nucleic acids, or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 nucleic acids, including any value within this range not explicitly recited herein, of the transgene of a donor DNA molecule and is capable of hybridizing to that region of the transgene of the donor DNA molecule. In some embodiments, the bait RNA may be substantially complementary to a fragment of the transgene of the donor DNA molecule.

In some embodiments, the invention provides the methods described above, further comprising introducing into the cell a third nucleic acid molecule comprising a nucleotide sequence encoding an anti-silencing polypeptide. In some embodiments, the anti-silencing polypeptide may be provided to the cell. In some embodiments, the anti-silencing protein is or is derived from a viral silencing suppressor (VSR). In further embodiments, the anti-silencing protein is a VSR derived from a plant virus. In further embodiments, the anti-silencing protein is the viral silencing suppressor p19 protein, derived from a Tombus virus, for example CymRSV, CIRV, or TBSV. Zhu et al recently showed that p19 VSR derived from Tomato Bushy Stunt Virus co-expressed with a guide RNA and a Cas9 nuclease improved gene targeting efficiency and/or guide RNA stability in plants (U.S. Patent Publication No. 2016/0264982). In some embodiments, the VSR is selected from the group of plant virus proteins including HC-Pro, p14, p38, NSs, NS3, CaMV P6, PNS10, P122, 2b, Potex p25, ToRSV CP, P0, and SPMMV P1 (see Csorba et al., 2015, Virology 479-480 p. 85-103, hereby incorporated by reference).

In some embodiments, the invention provides the methods described above where the method of the invention provides a higher frequency of recovered cells or events comprising the introduced transgene compared to a method which uses a guide RNA molecule that does not comprise a bait RNA. Therefore, the method may be described as an improvement over the art. The increase may be by at least 10%, at least 15%, at least 20%, at least 25%, at least 30%, at least 40%, at least 50%, at least 60%, at least 70%, at least 80%, at least 90%, at least 100%, at least 125%, at least 150%, at least 175%, at least 200%, at least 300%, at least 400%, at least 500%, at least 600%, at least 700%, at least 800%, at least 900%, or at least 1000% or greater compared to a method that comprises a guide RNA molecule that does not have a bait RNA.

In the methods herein wherein the first nucleic acid molecule comprises, for example, at least about 8 contiguous nucleotides having, for example, at least 70% identity with a target site in the genome of the cell, the first nucleic acid molecule is integrated into the genome of the cell via homologous recombination, thereby integrating the one or more transgenes into the genome of the cell.

In some embodiments, the invention provides a method of producing a plant, plant part, or progeny thereof comprising a transgene integrated into a targeted genomic site in the plant genome, where the method comprises regenerating a plant from the plant cell produced by the method described above. The invention further provides a plant, plant part, or progeny thereof comprising a transgene integrated into a targeted genomic site in the plant genome, produced by the method described above.

A chimeric RNA of the invention, comprising a guide RNA and a bait RNA, can also be used for targeted insertion of modified gene sequence targeted to a gene within the genome, which is also called allele replacement. Without being bound by theory, the modified gene sequence is highly homologous to the targeted genomic site, so that the modified gene sequence could replace at least a portion of the nucleotides of the targeted genomic site by homologous recombination via homology-dependent repair following RNA-mediated targeted genomic cleavage. Allele replacement does not introduce foreign gene sequences. Allele replacement typically involves precise replacement of at least one nucleotide to modify gene functions, such as enzymatic activity or a regulatory function. In some embodiments, allele replacement can be used to replace a few nucleotides of a coding region of a gene to produce a new functional protein or enzyme variants containing one or a few new amino acid changes. For example, a glyphosate sensitive EPSPS gene allele can be converted into a glyphosate tolerant variant by changing 2 amino acids, T178I and P182A mutation using CRISPR-Cas9 mediated genome editing (Sauer N J et al., 2016, Plant Physiol. DOI:10.1104/pp.15.01696). Allele replacement frequency is typically quite low in crop plants even with the use of site-directed nucleases to increase its frequency up to thousands of fold in comparison with background homology recombination frequency, thus making its application in crop improvement limited.

Despite the relatively low frequency of homology-dependent repair in higher plants, targeted allele replacement to recover herbicide resistance genome variants is relatively straightforward since the introduced herbicide tolerant variant can be directly selected and recovered. Unfortunately, for most agronomical important traits such as disease resistance, flowering time, drought tolerance and yield enhancement, there is no effective selection or even enrichment method to recover the desirable variants among hundreds or thousands of regenerated plant lines. Thus, broad application of homology dependent allele replacement is still limited by low frequency of homology-dependent repair in these applications where the target genes are not selectable. Therefore, there is a great need for an improved method for allele replacement which has a greater frequency of introducing the modified gene sequence via homologous recombination, so that fewer regenerated plant lines need to be screened and/or selected to recover the introduced gene modification(s).

The present invention provides a method of allelic replacement by nucleic acid modification of a target genomic site in a cell, whereby the target genomic site comprises at least a fragment of a native gene, comprising introducing into a cell: a) a first nucleic acid molecule comprising a donor DNA molecule, which comprises at least 10 contiguous nucleotides at least 80% identical to a genomic nucleic acid sequence, and further comprises a modified nucleic acid molecule comprising a nucleic acid sequence modified from the native gene; and b) a second nucleic acid molecule comprising a nucleotide sequence encoding a nuclease for site-directed cleavage at a target genomic site, and further comprising a nucleic acid sequence encoding a chimeric RNA of the invention, wherein the bait RNA is at least 70% complementary to at least 8 contiguous nucleotides of the modified nucleic acid sequence, under conditions where expression of the second nucleic acid molecule can occur to produce the nuclease and the nuclease can cleave the nucleotide sequence of the target genomic site, whereby the modified nucleic acid molecule is integrated at the target genomic site in the genome of the cell.

The present invention also provides a method of allelic replacement by nucleic acid modification of a target genomic site in a cell, whereby the target genomic site comprises at least a fragment of a native gene, comprising providing to the cell: a) a first nucleic acid molecule comprising a donor DNA molecule comprising a modified nucleic acid molecule comprising a nucleic acid sequence modified compared to the native gene, and said donor DNA molecule further comprising at least 10 contiguous nucleotides at least 80% identical to a genomic nucleic acid sequence, b) a second nucleic acid molecule comprising at least one nucleic acid sequence comprising a chimeric RNA of the invention, wherein the target nucleic acid sequence is the target genomic site of the cell, and c) a nuclease capable of site-directed cleavage at the target genomic site proximal to the genomic nucleic acid sequence of part a). These components are provided under conditions wherein the nuclease can cleave the nucleotide sequence of the target genomic site, whereby the modified nucleic acid molecule is integrated at the target genomic site in the genome of the cell and the targeted gene is replaced, thereby creating an allelic replacement. The second nucleic acid comprising the chimeric RNA of the invention may be pre-bound to the nuclease. Because the chimeric RNA comprises the bait RNA which is at least partially complementary to the donor DNA molecule, it is possible that the nuclease, chimeric RNA, and donor DNA are provided to the cell as a complex. This complex may be further complexed with other polypeptides, for example a Feldan shuttle.

The present invention also provides a method of allelic replacement by nucleic acid modification of a target genomic site in a cell, whereby the target genomic site comprises at least a fragment of a native gene, comprising providing to the cell: a) a first nucleic acid molecule comprising a donor DNA molecule comprising a modified nucleic acid molecule comprising a nucleic acid sequence modified compared to the native gene, and said donor DNA molecule further comprising at least 10 contiguous nucleotides at least 80% identical to a genomic nucleic acid sequence; b) a second nucleic acid molecule comprising at least one nucleic acid sequence comprising a chimeric RNA of the invention, wherein the target nucleic acid sequence is the target genomic site of the cell; c) a nuclease capable of site-directed cleavage at the target genomic site proximal to the genomic nucleic acid sequence of part a), and d) a RNA binding protein capable of binding to the chimeric RNA of part b), under conditions wherein the nuclease can cleave the targeted genomic nucleotide sequence at the target genomic site, whereby the transgene is integrated at the target genomic site in the genome of the cell. In some embodiments, the nuclease may be a site specific nuclease, such a meganuclease, a zinc finger nuclease, a TALEN, for a CRISPR-associated nuclease. In some embodiments, the RNA binding protein is a dCas9 ("dead" Cas9) or dCpf1 ("dead" Cpf1), wherein the nuclease activity of the RNA binding protein is inactivated.

In some embodiments of the methods of the invention of allelic replacement by nucleic acid modification of a target genomic site in a cell, the cell is a plant cell. In further embodiments, the cell is a monocotyledonous or dicotyledonous plant cell. In still further embodiments, the cell is a maize, rice, sorghum, sugarcane, barley, wheat, oat, turf grass, ornamental grass, tobacco, tomato, pepper, eggplant, sunflower, crucifer, flax, potato, cotton, soybean, sugar beet, or oilseed rape cell. In some embodiments, the first and/or second nucleic acid molecules may be introduced into the cell by biolistic nucleic acid delivery, via an *Agrobacterium*, by co-transformation, and/or with a T-DNA vector in any combination and/or order. In some embodiments, the first and second nucleic acid molecules are present on a single nucleic acid construct. In some embodiments, the first and second nucleic acid molecules are present on separate nucleic acid constructs. In other embodiments, the first and/or the second nucleic acid molecules are transiently expressed in the cell. In some embodiments, the first and/or the second nucleic acid molecules are stably transformed into a cell.

In some embodiments of the methods of the invention of allelic replacement by nucleic acid modification of a target genomic site in the genome of a cell, the chimeric RNA of the invention comprises a guide RNA and a bait RNA that is at least 8 contiguous nucleic acids and is at least 70% complementary to a fragment of the donor molecule consisting of a modified nucleic acid molecule comprising a nucleic acid sequence modified compared to the native gene. In other embodiments, the chimeric RNA of the invention comprises a guide RNA and a bait RNA that is at least 8 contiguous nucleic acids and is at least 70% complementary to the genomic nucleic acid sequence of part a) of the methods of the invention described above. In other embodiments, the chimeric RNA of the invention comprises a guide RNA and a bait RNA that is at least 70% complementary to at least 8 contiguous nucleic acids to a fragment of the donor DNA molecule, wherein the fragment is neither the modified nucleic acid molecule comprising a nucleic acid sequence modified compared to the native gene, nor the genomic nucleic acid sequence of part a) of the methods of the invention described above.

In some embodiments, the invention provides the methods described above where the first nucleic acid molecule comprising a donor DNA molecule may comprise at least 10 contiguous nucleic acids, wherein the nucleic acid molecule is at least 70% identical to a genomic nucleic acid sequence, such that these contiguous nucleotides are sufficient for homologous recombination of the donor DNA molecule, which further comprises a modified nucleic acid molecule compared to the native gene sequence, into the genome of the cell at the targeted genomic site following targeted nuclease cleavage. In other embodiments, a donor DNA molecule may comprise at least 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, or at least 1,000 contiguous nucleic acids, wherein said nucleic acid molecule is at least 70%, 75%, 80%, 85%, 86%, 87%, 88%, 89%, 90%, 91%, 92%, 93%, 94%, 95%, 96%, 97%, 98%, or at least 99% or 100% identical to a genomic nucleic acid sequence, and further comprise a transgene. In some embodiments, the donor DNA molecule may be substantially complementary to a genomic nucleic acid sequence. In some embodiments, the donor DNA molecule is single stranded. In other embodiments, the donor DNA molecule is at least partially double stranded.

In some embodiments, the method of allelic replacement is an improvement compared to the art. The improved method has a greater frequency of targeted allele replacement, which may be referred to as targeted allele replacement efficiency. This improved targeted allele replacement efficiency is an increase in targeted allele replacement efficiency, which is intended to mean that the number of cells or events recovered which comprise the modified nucleic acid molecule comprising a nucleic acid sequence modified compared to the native gene is increased relative to a similar method which comprises a guide RNA that does not have a bait RNA. The increase may be by at least 10%, at least 15%, at least 20%, at least 25%, at least 30%, at least 40%, at least 50%, at least 60%, at least 70%, at least 80%, at least 90%, at least 100%, at least 125%, at least 150%, at least 175%, at least 200%, at least 300%, at least 400%, at least 500%, at least 600%, at least 700%, at least 800%, at least 900%, or at least 1000% or greater compared to a method that comprises a guide RNA that does not have a bait RNA.

In some embodiments, the invention provides the methods described above where the second nucleic acid molecule encodes a site-directed modifying polypeptide. In further embodiments, the site-directed modifying polypeptide is a nuclease. In still further embodiments, the site-directed modifying polypeptide is a nuclease that is an endonuclease, for example a meganuclease, a zinc finger nuclease, or a TALEN. In some embodiments, the nuclease is an RNA-guided endonuclease.

In further embodiments, the nuclease is a CRISPR-associated nuclease, for example Cas9 or Cpf1 or a mutant variant of Cas9 or Cpf1, for example a nuclease-deactivated mutant variant, or a fusion between at least one domain of Cas9 or Cpf1 and at least one domain of a different site-directed modifying polypeptide.

In some embodiments, the invention provides the method described above where the second nucleic acid molecule further comprises a chimeric RNA which comprises a guide RNA and a bait RNA that is at least 8 or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 contiguous nucleic acids, including any value within this range not explicitly recited herein. The nucleic acid sequence of the bait RNA may be at least 70%, 75%, 80%, 85%, 86%, 87%, 88%, 89%, 90%, 91%, 92%, 93%, 94%, 95%, 96%, 97%, 98%, or at least 99% or 100% identical to at least 8 contiguous nucleic acids, or at least 9, 10, 11, 12, 13, 14, 15, 16, 17, 18, 19, 20, 22, 24, 25, 27, 29, 30, 32, 34, 36, 38, 40, 42, 44, 46, 48, 50, 52, 54, 56, 58, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 550, 600, 650, 700, 750, 800, 850, 900, 950, 1000, 1500, 2000, 2500, 3000, 3500, 4000, 4500, 5000, 7500, 10000, 15,000 or 20,000 nucleic acids, including any value within this range not explicitly recited herein, of the modified nucleic acid sequence of interest of the donor DNA molecule and is capable of hybridizing to that region of the donor DNA molecule. In some embodiments, the bait RNA may be substantially complementary to a fragment of the donor DNA molecule.

In some embodiments, the invention provides the methods described above, further comprising introducing into the cell a third nucleic acid molecule comprising a nucleotide sequence encoding an anti-silencing polypeptide. In some embodiments, the anti-silencing protein is or is derived from a viral silencing suppressor (VSR). In further embodiments, the anti-silencing protein is a VSR derived from a plant virus. In further embodiments, the anti-silencing protein is the viral silencing suppressor p19 protein, derived from a Tombus virus, for example CymRSV, CIRV, or TBSV. Zhu et al recently showed that p19 VSR derived from Tomato Bushy Stunt Virus co-expressed with a guide RNA and a Cas9 nucleease improved gene targeting efficiency and/or guide RNA stability in plants (U.S. Patent Publication No. 2016/0264982). In some embodiments, the VSR is selected from the group of plant virus proteins including HC-Pro, p14, p38, NSs, NS3, CaMV P6, PNS10, P122, 2b, Potex p25, ToRSV CP, P0, and SPMMV P1 (see Csorba et al., 2015, Virology 479-480 p. 85-103, hereby incorporated by reference).

In some embodiments, the invention provides the methods described above where the method of the invention provides a higher frequency of recovered cells comprising the introduced modified nucleic acid sequence compared to a method which uses a guide RNA that does not comprise a bait RNA.

In some embodiments, the invention provides a method of producing a plant, plant part, or progeny thereof comprising a modified nucleic acid sequence molecule integrated into a targeted genomic site in the plant genome, thereby producing an allelic replacement, where the method comprises regenerating a plant from the plant cell produced by the methods of allelic replacement described above. The invention further provides a plant, plant part, or progeny thereof comprising a modified gene integrated into a targeted genomic site in the plant genome, produced by the methods described above.

The present invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the present invention.

EXAMPLES

Although the foregoing invention has been described in some detail by way of illustration and example for purposes of clarity of understanding, it will be apparent that certain changes and modifications may be practiced with the scope of the present invention.

Example 1: Homology-Dependent Targeted Insertion of Transgenes is Enhanced by the Use of Guide RNA Molecule Containing Bait Sequences To test if CRISPR-Cas9 vector expressing a single guide RNA (sgRNA) containing extra "bait" RNA sequences hybridizing with donor DNA (FIG. 1) is able to recruit the donor molecules to the chromosomal breaks for target insertion and thus improving the overall targeted transformation efficiency, the following expression vectors were constructed and side-by-side targeted insertion experiments were performed using biolistic bombardment delivery.

1.1: Construction of Vectors for Cas9 and Chimeric Guide-Bait RNA Expression and Donor Vector for Targeted Transgene Insertion in Maize Construction of Cas9 expression vectors and targeting donors have been described before (WO16106121, incorporated by reference in its entirety herein). The maize-optimized Type II Cas9 gene from *Streptococcus pyogenes* SF370 (cBCas9Nu-01) was driven under the control of maize ubiquitin-1 promoter (prUbi1-10) followed by NOS terminator. A nuclear localization signal was also incorporated into the C-terminus of Cas9 to improve its targeting to nucleus. Vector 22169 has been described previously site and are useful for guiding targeted insertion of the donor molecule to the Cas9 cleavage site of the target genomic site, where insertion may occur by a mechanism which includes homologous recombination.

TABLE 1

Vectors for targeted transgene insertion

| Vector ID | Expression Cassettes | Description | SEQ ID NO[1] |
|---|---|---|---|
| 22169 | prUbi1-10:cBCas9Nu-01:tNOS-5-1; prOsU3-01:xZmMIR604FR2:rsgRNAZmMIR604FR2-01 | Cas9 nuclease; sgRNA | 8, 9 |
| 23306 | prUbi1-10:cBCas9Nu-01:tNOS-5-1; prOsU3-01:xZmMIR604FR2:rsgRNAZmMIR604FRxPMI-01 | Cas9 nuclease; sgRNA with bait RNA | 8, 10 |
| 23576 | prUbi1-10:cBCas9Nu-01:tNOS-5-1; prOsU3-01:xZmMIR604FR2:rsgRNAZmMIR604FRxPMI-01; prOsU6-01:xZmMIR604FR2:rsgRNAZmMIR604FR2-01 | Cas9 nuclease; sgRNA with bait RNA; sgRNA | 8, 9, 10 |
| 23309 | xJHAX-03:prUbi1-10:cPMI-09:tNOS-05-01:xJAX-04 | targeted insertion donor | 11 |

[1]SEQ ID NO of expression cassettes only (WO16106121) and was used as a control for experiments as vector with no bait sequence in its sgRNA. MIR604FR2 (5'-AGTGC AGTGC AGTGC AG/GAC AGG-3', SEQ ID No. 1, "/" denotes the cleavage site and the last 3 nucleotide AGG serves as the PAM sequence) was chosen as a target genomic site for testing Cas9-gRNA mediated transgene insertion. MIR604FR2 is located within the MIR604 event insertion site locus (U.S. Pat. Nos. 7,316,813; 7,897,748, and 8,354,519, incorporated by reference in its entirety herein), for example in elite maize variety NP2222. Briefly, vector 22169 comprises an expression cassette which expresses a sgRNA that can guide Cas9-medaited cleavage of target genomic sequence MIR604FR2 (SEQ ID NO: 1). The sgRNA expression cassette comprises rice U3 promoter (prOsU3) operably linked at the 3' end to coding sequences for the sgRNA rsgRNAZmMIR604FR2 (SEQ ID No. 3). rsgRNAZmMIR604FR2 comprises a 19-nt specificity-conferring targeting RNA xMIR604FR2 (SEQ ID No. 2) linked to the crRNA and tracrRNA scaffold sequences for interaction with Cas9. The expression cassette comprising prOsU3 promoter and sgRNA rsgRNAZmMIR604FR2 (SEQ ID No. 3) was cloned into a biolistic transformation vector along with the Cas9 expression cassette to form vector 22169.

A vector for expressing a chimeric sgRNA comprising a bait RNA capable of hybridizing with donor DNA sequences was created. The bait RNA is a 190 nucleotide PMIRV sequence (SEQ ID No. 4). Vector 23306 comprises the PMIRV sequence linked at its 5' end to the sgRNA cassette of 22169, and operably linked at its 3'-end to the polyT termination signal. In comparison with 22169, the sgRNA rsgRNAZmMIR604FR2 has been replaced with sgRNA-rsgRNAZmMIR604FR2PMI (SEQ ID No. 5; comprises bait RNA segment SEQ ID NO: 4) in vector 23306.

Control vector 23576 comprises expression cassettes capable of expressing both a sgRNA without a bait RNA segment and a sgRNA with a bait RNA segment. Donor vector 23309 comprises a PMI expression cassette, which encodes for the selectable marker phosphomannose isomerase and provides the ability to metabolize mannose (U.S. Pat. Nos. 5,767,378 and 5,994,629, incorporated by reference herein). The PMI expression cassette is linked at the 5' end to JHAX-03 (SEQ ID No. 6) and at the 3' end to xJHAX-04 (SEQ ID No. 7). These 2 kb and 1 kb fragments of nucleotide sequence are homologous to the MIR604 region of NP2222 maize genome, and are referred to as the "homologous arms" of the MIR604 targeted genomic insertion site. The sequences of these two homologous arms are identical to part of the MIR604 targeted genomic insertion 1.2: Generation of Targeted Insertion Events at the MIR604 Insertion Site Using Biolistic Bombardment To generate potential events carrying targeted insertion at the MIR604 insertion site, elite maize transformation variety NP2222 was chosen for all experiments as described (WO16106121, incorporated by reference herein). Methods for maize immature embryo bombardment, callus induction and selection, plant regeneration and rooting have been described previously (Wright et al., 2001, Plant Cell Reports 20:429-436). Briefly, immature embryos were isolated from sterilized immature ears of elite maize variety NP2222 at 9-11 days after pollination, and pre-cultured for 1 to 3 days on osmoticum media. Plasmid DNA of vector 22169 or 23306 was mixed with a donor fragment from vector 23309. The DNA mixture was then co-precipitated onto gold particles and used to bombard pre-cultured embryos. After bombardment with the DNA-gold particles using BioRad PDS-1000 Biolistic particle delivery system as described, bombarded embryos were then incubated in callus induction media and then moved onto mannose selection media. Mannose resistant calli were selected to regeneration media for shoot formation. Shoots were then sub-cultured onto rooting media. Samples were then harvested from rooted plants for Taqman assays.

TaqMan assays were performed to enrich for potential targeted insertion events. This analysis enabled the removal of events with no target site modification and also those events which possessed only a small deletion of the target locus next to the nuclease cleavage site. TaqMan analysis was essentially carried out as described in Ingham et al. (Biotechniques 31(1):132-4, 136-40, 2001), herein incorporated by reference. TaqMan assay 1 (primer sequences are SEQ ID NO: 12 and 13, probe sequence is SEQ ID NO: 14) is for assaying target site cleavage by the nuclease and is an indicator of nuclease activity. TaqMan assay 2 (primer sequences are SEQ ID NO: 15 and 16; probe sequence is SEQ ID NO: 17) is for assaying cleavage of the targeted locus away from the nuclease cleavage site. For both assays, a targeted insertion event must have a 0 or 1 copy number call, although a 0 or 1 copy number call does not necessary mean the event has the targeted insertion.

Following the enrichment of events which potentially contained the targeted insertion, 2 different PCR assays were performed at the junctions of the inserted sequence and target genomic site to identify potential plants containing the targeted insertion. Primers sequences for junction PCR 1 are SEQ ID NO: 18 and 19; primer sequences for junction PCR 2 are SEQ ID No: 20 and 21. These analyses determined the likely presence of a targeted insertion at the target genomic site. Double crossover recombinants, which comprise the insertion sequence, are positive for both PCRs. Identified putative targeted insertion events were further characterized by more detailed PCR, sequencing and Southern analysis for confirmation as described before (WO16106121, incorporated by reference herein).

Table 2 shows a side-by-side comparison experiment that resulted in significant improvement of targeted insertion frequency using sgRNA comprising a fusion of guide RNA with bait RNA which can hybridize with donor DNA and recruit the hybridized donor molecule to the chromosomal breaks. In treatment B which employs vector expressing a fusion RNA comprised of sgRNA and bait RNA, 5 targeted insertion events were recovered that were the results of precise double crossover homologous recombination (HR). The targeted insertion frequency is up to 0.13%, i.e. more than 1 targeted transgene insertion event could be generated from 1000 bombarded immature embryo explants of elite maize line NP2222. On the contrary, in control experiment A which uses regular sgRNA with no bait sequence present, no targeted events was recovered. In treatment C which uses a CRISPR vector expressing both sgRNA and sgRNA-bait fusion, no increase in targeting efficacy was observed, suggesting the interference effect of the regular sgRNA on recruiting the donor DNA molecules.

TABLE 2

Comparison of target transformation experiments using sgRNA-Cas9 with or without recruiting RNA targeting at the MIR604 insertion site target sequence MIR604FR2 in maize

| Treatment | A | B | C |
| --- | --- | --- | --- |
| DNA used for bombardment (1:1, 1 × 1010 molecules of each) | 22169, 23309 | 23306, 23309 | 23576, 23309 |
| No. of embryos | 1980 | 3735 | 2140 |
| Total transgenic events | 177 | 281 | 110 |
| Events with target site mutation | 170 | 249 | 46 |
| Events with confirmed targeted insertion | 0 | 5 | 0 |
| Precise targeted insertion frequency | 0.00% | 0.13% | 0.00% |

A more detailed molecular analysis of events from both treatments were performed (Table 3). In this set of side-by-side comparison experiment, both treatment A and B resulted in high frequency of modification of genomic target sequence MIR604FR2 in transgenic events selected on mannose (i.e. positive for PMI donor nucleic acid expression cassettes) (Table 2 and Table 3). These results indicate that addition of bait RNA sequence to the 3'-region of the tracrRNA does not significantly sgRNA function and impact Cas9-medaited cleavage. In control treatment A, 9 candidate targeted insertion events (5.1%) were identified from 177 events positive for donor vector (PMI). Among them, only two events did not have co-integrated Cas9 nuclease vector. Surprisingly, in 11 candidate targeted insertion events (3.9%) recovered from 281 donor positive events generated with chimeric sgRNA-bait fusion vector 23306 (Treatment B), 5 events did not contain a co-integrated Cas9 nuclease expression vector 23306.

TABLE 3

Breakdown of different types of events in regenerated plants using sgRNA-Cas9 with or without recruiting RNA targeted at the MIR604 insertion site target sequence MIR604FR2

| | Experiment ID | | | |
| --- | --- | --- | --- | --- |
| | Treatment A | | Treatment B | |
| | CRISPR-Cas9 vector | | | |
| | 22169 | | 23306 | |
| | Donor | | | |
| | 23309 | | 23309 | |
| | Event Number | % | Event Number | % |
| Total immature embryo targets | 1980 | | 3735 | |
| Total regenerated events | 255 | | 403 | |
| I). Donor vector (PMI) positive events | 177 | 8.9% | 281 | 7.5% |
| Donor positive events with co-integrated Cas9 vector | 146 | 81.5% | 173 | 61.5% |

TABLE 3-continued

Breakdown of different types of events in regenerated plants using sgRNA-Cas9 with or without recruiting RNA targeted at the MIR604 insertion site target sequence MIR604FR2

| | Experiment ID | | | |
|---|---|---|---|---|
| | Treatment A | | Treatment B | |
| | CRISPR-Cas9 vector | | | |
| | 22169 | | 23306 | |
| | Donor | | | |
| | 23309 | | 23309 | |
| | Event Number | % | Event Number | % |
| Donor positive events without co-integrated Cas9 vector | 31 | 17.5% | 108 | 38.4% |
| Donor positive events with target site modification | 170 | 96% | 238 | 84.7% |
| Candidate Donor positive events positive for targeted insertion | 9 | 5.1% | 11 | 3.9% |
| Confirmed events positive for targeted insertion without co-integrated Cas9 vector | 0 | 0% | 5 | 1.8% |
| II). Breakdown of donor positive events with target site modification | 170 | 96.0% | 238 | 84.7% |
| Donor positive events with monoallelic modification | 10 | | 16 | |
| Monoallelic modification with co-integrated Cas9 vector | 9 | | 7 | |
| Monoallelic modification without co-integrated Cas9 vector | 1 | | 9 | |
| Donor positive events with biallelic modifications | 160 | | 222 | |
| Biallelic modification with co-integrated Cas9 vector | 137 | | 147 | |
| Biallelic modification without co-integrated Cas9 vector | 23 | | 75 | |
| III). Donor vector (PMI) negative plants (Escapes) | 78 | 30.6% | 122 | 30.3% |
| Escapes with no target site modification | 55 | | 105 | |
| Escapes with target site modification | 23 | 29.5% | 17 | 13.9% |
| Total number of events with mutations at the target site | 193 | 75.7% | 255 | 63.3% |

Since transformation experiments in Tables 2 and 3 were done through co-delivery of repair donor and Cas9 nuclease expression constructs, it is expected to recover transgenic plants that do not contain a co-integrated Cas9 expression vector. The presence of target site (MIR604FR2) mutations in regenerated plants that escaped the mannose selection process (aka. transformation escapes) that do not contain nucleic acid sequence from either donor or Cas9 expression vectors were also screened for. Escape frequency in the experiments was about 30% using Cas9 nuclease with or without recruiting RNA (Table 3). Out of 78 escapes events from the experiment using control vector 22169 (Treatment A), a surprisingly high percentage of escape plants (29.5%) contained mutations at the genomic target site (MIR604FR2) sequence. Seven of these 23 events have mutation in one of the MIR604FR2 copies in the maize genome. The remaining 16 events have mutation in both copies of the sequence and one of these 16 events has co-integrated Cas9 nuclease expression vector. In comparison, only 13.9% of escape plants (17 out of 122 plants) negative for any transgene have mutations at the genomic target site (MIR604FR2) sequence using 23306 which expresses the chimeric guide-bait RNA fusion for recruiting donor DNA. Eleven and six events have a mutation in one of or both copies of the genomic target site MIR604FR2 sequence, respectively (Table 3).

The results shown above indicate that use of a chimeric RNA molecule comprising a guide RNA and a bait RNA for recruiting donor molecules to the Cas9 nuclease cleavage site can significantly improve homology-dependent gene targeting efficiency. It should be noted that the same principle can be applied to other RNA-guided nuclease systems which comprise other site-directed modifying polypeptides, such as Cpf1, or a mutant variant of Cas9 or Cpf1, such as the fusion dCas9-FokI polypeptide. Also, a nickase such as Cas9D10A can be used in place of the wild type double strand break nuclease Cas9. Alternatively, a dCas9-guided bait RNA can be used in combination with other site-directed nucleases such as TALEN or ZFN for recruiting donor DNA molecules to or proximal to the cleavage site of these nucleases.

1.3 Homology-Dependent Targeted Insertion of Transgenes Using the CRISPR-Cpf1 System with a Chimeric RNA Comprising a Guide RNA and a Bait RNA Segment Construction of vectors for a Cpf1 and a chimeric RNA comprising a guide RNA and a bait RNA (or without a bait RNA, as a control) is based on Example 1.1 and what is known in the art regarding the CRISPR-Cpf1 system, see for example Tang et al., 2017, Nature Plants, 3: Article No. 17018, Kim et al., 2017, Nature Communications, 8: Article No. 14406, Xu et al., 2016, Plant Biotechnology J., doi: 10.1111/pbi.12669 Zetsche et al., 2015, Cell, 163: 759-771, and U.S. Patent Publication US2016/0208243, all of which are incorporated by reference herein. Preferably, an expression cassette comprising a Cpf1 gene encoding a mutant Cpf1 enzyme with inactivated RNase activity is provided, and a second expression cassette encoding for a chimeric RNA comprising a guide RNA and a bait sequence. The mutant Cpf1 may be an AsCpf1 mutant, for example an AsCpf1 comprising at least one of the following mutations: H800A, K809A, K860A, F864A, and/or R790A. The mutant Cpf1 may also be an LbCpf1 mutant, for example an LbCpf1 comprising at least one of the following mutations: H843A, K852A, K869A, and/or F873A. Each of these Cpf1 mutants have completely lost their CRISPR array processing but have little or no impact on their DNA cleavage activity (Zetsche et al., 2015, Cell 163:1-13; Fonfara et al., 2016, Nature 532:517-521; Bayat et al., 2018, Current Microbiology 75:107-115, all herein incorporated by reference). Also, because Cpf1's PAM site is located upstream of the target recognition sequence of crRNA, the bait RNA sequence is preferably placed upstream of the crRNA scaffold so it does not interfere either with Cpf1 binding with the chimeric bait-crRNA or with Cpf1 recognition of PAM site. Plant cells are transformed using biolistic bombardment, similar to as described in Example 1.2, or *Agrobacterium*-mediated transformation using methods known in the art. Recovered transformed plant cells are assayed for the presence of the targeted mutation as described in Example 1.2.

1.4 Generation of Targeted Insertion Using a Dual Guide RNA

It is well-known in the art that CRISPR-Cas systems naturally occur with multiple RNA molecules making up the guide RNA. In this example, a dual-guide RNA strategy is used, where one RNA molecule comprises the crRNA and a second, physically distinct RNA molecule comprises the tracrRNA, which is operably linked to the bait RNA. Both crRNA and the chimeric tracrRNA-bait RNA can be expressed from the same DNA vector using any of the multiplex gRNA expression vector systems (for example, Lowder et al., 2016, Frontiers in Plant Science, doi.org/10.3389/fpls.2016.01683; Cermak et al., 2017, Plant Cell, doi.org/10.1105/tpc.16.00922, all incorporated by reference herein). Plant cells are transformed using biolistic bombardment, similar to as described in Example 1.2, or *Agrobacterium*-mediated transformation using methods known in the art. Recovered transformed plant cells are assayed for the presence of the targeted mutation as described in Example 1.2.

1.5 Generation of Targeted Insertion Using dCas9 or dCpf1 in Combination with Alternate Nuclease for Target Site Cleavage It is well known that dCas9 or dCpf1 (dead Cas9 or Cpf1 protein with inactivated nuclease domains) can still bind to guide RNAs (either a single RNA guide or dual-guide RNA for Cas9). In this example, an alternate nuclease such as TALEN or meganuclease (as described in WO16106121, incorporated by reference herein) is used to cleave a genomic target site (MIR604FR2) sequence. Guide RNA comprising spacer RNA targeting the MIR604 event insertion site locus and a bait RNA capable of hybridizing to a DNA donor is co-expressed with a dCas9 or dCpf1 protein from an expression vector in maize cells. The donor DNA molecule is also co-transformed into maize cells. Plant cells are transformed using biolistic bombardment, similar to as described in Example 1.2, or *Agrobacterium*-mediated transformation using methods known in the art. Recovered transformed plant cells are assayed for the presence of the targeted mutation as described in Example 1.2.

Example 2: Enhancement of Homology-Dependent Precise Genomic Sequence Replacement by Use of Chimeric RNA Molecule Containing Bait Sequences The following examples demonstrate that a chimeric RNA molecule comprising a guide RNA and a bait RNA segment increases the efficiency of donor molecule integration, possibly by homologous recombination via homology-dependent repair following RNA-guided cleavage of a target genomic site. A gene of interest is selected to illustrate the principle that a guide RNA molecule comprising a bait RNA segment can be used to greatly enhance homology-dependent precise genomic sequence replacement relatively to a system in which the guide RNA does not comprise a bait RNA segment. DNA vectors and transformation methods for achieving targeted mutagenesis and allele replacement using CRISPR-Cas9 system in said gene of interest have been described previously (WO16106121, incorporated in its entirety by reference herein).

Since donor DNAs used for allele replacement typically are very similar to the genomic target sequences to be edited, the choice of sequences for the design of bait RNA is limited. We developed two design approaches to maximize interaction between donor DNA and bait RNA sequences present in a single guide RNA. The first strategy is to design bait sequence against the portion of donor molecule that is different from the target sequence as shown in FIG. 1. In order to achieve specific donor recruitment, the donor molecules can be modified with silent mutations so the bait RNA will only hybridize to a particular segment of the donor, and not to the genomic target sequence. Additionally, natural intraspecies sequence variations which are not likely to unintentionally affect the expression or the performance of the targeted gene can be incorporated into the donor design to decrease the sequence identity between the donor DNA sequence and the target DNA sequence. For example, there are many single nucleotide polymorphisms (SNPs) between genomes of diverse germplasm and these natural polymorphisms can be incorporated into, for example, donor molecules for allele replacement in NP2222, the elite maize transformation line used in this study. In this example, SNPs from B73 can be incorporated into donor molecules so they are recruited by gRNA with the corresponding nucleotide sequences for targeted allele replacement in NP2222 maize cells.

As an example, maize native gene Bx9 was identified as a target to demonstrate the use of a bait RNA to recruit a donor molecule that contains engineered synonymous mutations for achieving allele replacement. Bx9 encodes a glucosyltransferase that catalyzes last biosynthesis step for benzoxazinoids, a class of abundant secondary metabolites found mainly in Gramineae including major crops maize and wheat (Rad et al., 2001, Plant Journal 28:633-642). Benzoxazinoids are the causal phytotoxic compounds contributing to the allelopathic effect of rye and corn and they can be used as weed control in organic farming (Schulz et al., 2013, J Chem Ecol 39:154-174). Bx9-encoded glucosyltransferase is also involved in detoxification of a synthetic photosystem II (PSII) inhibitor compound Apollo. In order to increase resistance of maize plant against the Apollo herbicidal compound, a mutant (A334K) is introduced into the endogenous Bx9 gene by homology-dependent repair mediated by CRISPR-Cas9 cleavage of the wild type Bx9 target sequence.

In the wild type Bx9 gene of maize variety NP2222, target region sequence 5'-CGC GGC CGT GGC ATC GTC GTC ACC TGG GCG CCG CAG GAG GAG-3' (SEQ ID NO: 22) encodes the following amino acid sequence RGRGIV-VAWAPQEE (SEQ ID NO: 23). To increase targeted editing frequency resulting in A334K mutation, transformation vector pInBx9A334, which is similar to the previously described vector 23306, is constructed for expression of Cas9 and a sgRNA to target cleavage of the Bx9 gene sequence. In pInBx9A334, the sgRNA contains two unique segments; one is the Bx9 targeting sequence (5'-GGC CGT GGC ACG TCG TCA CC-3', SEQ ID NO: 24) to guide Cas9 cleavage of the Bx9 target sequence and the other is the bait RNA segment (5'-ttC tTC tTG gGG aGC CCA ctt cAC aAC tAT aCC tCt aCC tCt-3', SEQ ID NO: 25, in the non-coding strand and mutated nucleotides in lower case) for hybridizing with the donor oligonucleotide molecule. A 108 bp donor oligonucleotide containing the A334K mutation and other synonymous mutations (5'-CCC GAC GGG GTG GAG GAC GAG GTG aGa GGt aGa GGt ATa GTt GTg aag TGG GCt CCc CAa GAa Gaa GTG CTC GCG CAC CCG GCC GTC GGC GGC TTC CTC ACC CAC AAC-3', SEQ ID NO: 26, in the coding strand and mutated nucleotides in lower case) is used to generate edited lines with desired A334K replacement. This donor sequence contains 3 mutant nucleotides encoding the desired A334K mutations and additional silent mutations (5'-aGa GGt aGa GGt ATa GTt GTg aag TGG GCt CCc CAa GAa Gaa-3', SEQ ID NO: 27, mutant nucleotides in lower case). This mutated sequence encodes a mutant peptide, RGRGIVVKWAPQEE, (SEQ ID NO: 28, the mutant lysine (K) residue is underlined). It should be noted that the donor DNA molecule can be single strand oligonucleotide, partially or completely double strand DNA fragments. Also, the length of homology regions flanking the bait-hybridizing (or prey) sequences can be increased or decreased as needed. pInBx9A334 and donor oligonucleotide (SEQ ID NO: 26) are co-delivered into immature maize embryos using biolistic bombardment, as described in Example 1.2. The resulting immature embryos are then incubated in callus induction and regeneration media to generate mutant plant lines. Leaf tissues are removed from the recovered plant cells for a genotyping assay to identify the presence of the desired A334K mutation, similar to the TaqMan assay described in Example 1.2.

Another design to maximize interaction between bait RNA sequence of the guide RNA and donor molecule is to use a universal bait as shown in FIG. 2. In this design, a gRNA molecule, for example an isolated gRNA molecule or a gRNA molecule expressed by an expression vector, comprises a given bait RNA sequence (referred to as a "universal bait RNA sequence" or "universal bait RNA") and different DNA donor molecules may each be linked to the corresponding complementary, or at least 80% complementary, prey sequence (referred to as a "universal prey sequence"). The bait RNA may be at least 8 nucleic acids in length. For example, the PMIRV bait (SEQ ID NO: 4), which is 190 nucleotides in length, or the 150 nucleotide long yeast ADH1 gene sequence, xScADH1 (SEQ ID NO: 29), can be used as universal bait RNA to recruit any donor DNA molecules containing universal prey sequences capable of hybridizing to the universal bait RNA. The universal prey sequence, which hybridizes to the bait RNA, can be linked to different donor DNA molecules at the 5' end, thus leaving the free 3'-end for searching homology and initiating homology-dependent repair with genomic target sequences. Alternatively, the universal prey sequence may be linked to the 3' end of the donor DNA molecule. The length of the prey sequence can be adjusted based on the nature of the donor, but may be at least 8 nucleic acids in length and/or at least 80% complementary to the universal bait RNA. For example, when a donor DNA molecule is delivered as a T-DNA by *Agrobacterium*-mediated transformation, longer prey sequences can be used; however, when a donor DNA is synthesized chemically, it may be more cost effective to use a shorter prey nucleic acid sequence to reduce the cost of DNA synthesis. Additionally, more than one universal bait RNA sequence may be linked to form a gRNA molecule comprising multiple bait RNAs for recruiting multiple donor DNA molecules to target multiple genes.

As an example of using universal bait design, we designed a gRNA to introduce the A334K mutation into the endogenous Bx9 gene of maize variety NP2222 for increasing resistance of the maize variety against the Apollo herbicidal compound using Cas9-mediated homology-dependent repair (HDR). To guide cleavage of Bx9 gene close to the A334 coding sequence and to recruit the donor molecule to the Bx9 cleavage site, an expression vector pBxA334ScAdh is constructed. pBxA334ScAdh is similar to the previously described binary vector 23306 and comprises two expression cassettes, one for expression of a Cas9 nuclease and another for expression of the chimeric RNA rsgR-NAZmBx9-08 (SEQ ID NO: 30) containing the xScADH1 (SEQ ID NO: 29) bait sequence located downstream of the tracrRNA segment. In order to generate mutant lines with the Bx9 gene A334K mutation, immature maize embryos are bombarded with pBxA334ScAdh along with donor DNA molecules containing its corresponding prey sequence xScAdh1RV (SEQ ID NO: 31) fused to the 5'- or 3'-end of the mutant Bx9 donor DNA (SEQ ID NO: 32). For example, the prey sequence (SEQ. ID. NO: 31) may be fused to the 5'-end of SEQ ID NO: 32, thereby creating a new donor molecule (SEQ ID NO: 33). The new donor molecule (SEQ ID NO: 33) is complementary to the genomic Bx9 target sequence as well as the universal bait RNA sequence xScADH1 for recruitment of the repair donor DNA molecule to the target genomic site. The donor molecule comprising SEQ ID NO: 33 can be chemically synthesized as single stranded DNA or be cloned into a plasmid vector to form dsDNA. Donor molecules in ssDNA or dsDNA form are co-delivered into maize cells along with Cas9 and chimeric RNA (comprising the guide RNA and the bait RNA) expression vector pBxA334ScAdh using either biolistic delivery or *Agrobacterium*-mediated transformation as described above. The resulting immature embryos are then incubated in callus induction and regeneration media to generate mutant plant lines. Leaf tissues are removed from the recovered plant cells for TaqMan genotyping assay for the presence of the desired A334K mutation as described in Example 1.2.

What is claimed is:

1. A chimeric RNA for targeted genomic modification of a cell, wherein the chimeric RNA comprises:
   a) a guide RNA comprising a polynucleotide targeting guide sequence of at least 8 contiguous nucleotides and at least 80% identical to a target nucleic acid sequence of at least 8 contiguous nucleotides within a target nucleic acid molecule; and
   b) a bait RNA comprising at least 8 contiguous nucleic acids, wherein the nucleic acid sequence of the bait RNA is at least 70% complementary to at least 8 contiguous nucleic acids of a donor DNA molecule, wherein the donor DNA molecule is intended for integration into the genome of a cell, wherein a tracrRNA is operably linked to said bait RNA sequence.

2. The chimeric RNA of claim 1, wherein said bait RNA is operably linked to said guide RNA.

3. The chimeric RNA of claim 2, wherein the guide RNA further comprises a nucleic acid sequence which is a binding site for a site-directed modifying polypeptide.

4. The chimeric RNA of claim 1, wherein the guide RNA comprises a crRNA.

5. The chimeric RNA of claim 4, wherein the crRNA is operably linked to said bait RNA.

6. The chimeric RNA of claim 1, wherein the guide RNA comprises a crRNA operably linked to said tracrRNA.

7. The chimeric RNA of claim 1, wherein the guide RNA further comprises a tracrRNA, wherein the tracrRNA interacts with the guide RNA to create an RNA duplex that is a binding site for a site-directed modifying polypeptide.

8. The chimeric RNA of claim 7, wherein the guide RNA comprises a tracrRNA operably linked to a bait RNA.

9. An expression cassette comprising a nucleic acid sequence encoding the chimeric RNA of claim 1.

* * * * *

SEQUENCE LISTING

```
<160> NUMBER OF SEQ ID NOS: 33

<210> SEQ ID NO 1
<211> LENGTH: 23
<212> TYPE: DNA
<213> ORGANISM: Zea mays

<400> SEQUENCE: 1
agtgcagtgc agtgcaggac agg                                           23

<210> SEQ ID NO 2
<211> LENGTH: 19
<212> TYPE: DNA
```

<213> ORGANISM: Zea mays

<400> SEQUENCE: 2
gtgcagtgca gtgcaggac        19

<210> SEQ ID NO 3
<211> LENGTH: 105
<212> TYPE: DNA
<213> ORGANISM: Artificial Sequence
<220> FEATURE:
<223> OTHER INFORMATION: Zea mays, Streptococcus pyogenes

<400> SEQUENCE: 3
agtgcagtgc agtgcaggac gttttagagc tagaaatagc aagttaaaat aaggctagtc        60
cgttatcaac ttgaaaaagt ggcaccgagt cggtgctttt ttttt        105

<210> SEQ ID NO 4
<211> LENGTH: 190
<212> TYPE: DNA
<213> ORGANISM: Artificial Sequence
<220> FEATURE:
<223> OTHER INFORMATION: Escherichia coli, Zea mays

<400> SEQUENCE: 4
acgggctgca gcaggctcac gatctcgctg aactcgcgga aggcgttcat ggccaggaag        60
ggggtcaggg cgaacaccag ctcgggcttg tggttgggt ccttgtagtt gcgctcggcg        120
gcgtccatgg ggatgccggc ggcgttctcc ttggcgaagc cgatctcgct gttgtgcttg        180
ttggggtgca        190

<210> SEQ ID NO 5
<211> LENGTH: 295
<212> TYPE: DNA
<213> ORGANISM: Artificial Sequence
<220> FEATURE:
<223> OTHER INFORMATION: S. pyogenes, Z. mays, E. coli

<400> SEQUENCE: 5
agtgcagtgc agtgcaggac gttttagagc tagaaatagc aagttaaaat aaggctagtc        60
cgttatcaac ttgaaaaagt ggcaccgagt cggtgcacgg gctgcagcag gctcacgatc        120
tcgctgaact cgcggaaggc gttcatggcc aggaaggggg tcaggcgaa caccagctcg        180 ggcttgtggt tgggtccctt gtagttgcgc tcggcggcgt ccatggggat gccggcggcg        240
ttctccttgg cgaagccgat ctcgctgttg tgcttgttgg ggtgcattt ttttt        295

<210> SEQ ID NO 6
<211> LENGTH: 1995
<212> TYPE: DNA
<213> ORGANISM: Zea mays

<400> SEQUENCE: 6
aacgagaata atgtcgtcat cttcgacctc gacggcggta cctttgacgt cgcgctccgg        60
cggctaagga ccgcactgcc gacgagggca tgagtggcgc cgagatggaa gagaagagga        120
gcacaaatgg cggtcgtcgg caaagacaaa gagaactcga gcgtgagtgg aggaaggggc        180
aaatgtgtaa ctccagcttg gatatgactc cactgaccag attacgagcg acatcaacta        240
gattgtgtgt ctcagtggct cagtgccatt ttttgaggtt tgggtgccaa tattttttcg        300
tagtggaagg caccgcgccc atcgggtttt gggagccaaa cgccaaaccc gctcgcctca        360
tattccgcaa cgtacagcgg tttcatgggc tggttgaagg cccgggccgc aaaccaaccg        420

```
agtcgggccg acgccctggg agatccgcac ggctggtctg gcccaagcaa cctggtgggt    480
tggtgccagg ttacagcctg ggctgatctg tggacggtgg accatgcaag gttgtactgg    540
gcttgcaagg ttgtactggg cctactggaa cagtcatagc ccgtgccgtc gtggtgaccg    600
tcgtacgcgg ccgatctggc agactgggca ggtcgctgct ccgtgctgtt tgtggatgca    660
atgcaactat gcaagagtga tcacggaaaa cggacggagc ctgtctgtcc tgttgcgacg    720
tagtacaagc gcctgaacag tgacgctacg ctatgccacg agcctacgag tggtaggtag    780
tagtacactg gtcagaatcc agcagtgcac ccacgccgct gctgactttg ctgatgagag    840
ggaggggtcg agcgagtctg tgtgaaaccg tgaaccccgc cggggccttc agtacgtacg    900
ataccacgag cagtagaaaa aacaacgcca agatggcaga gtcaacaacc gatcacagta    960
cgtatcgcat tcacatcaag attttaagaa cgacccccgg ctggccaatg caggccact   1020 tggttgcccg tgcccgacag agggacacgg cgccatgccc tccgcgccgc acggacgagg   1080
tgtcgtgaga accggcaaaa aaaaaaatca tcgcaagtgc gctgaagtga agtgccttcc   1140
cccgcgtttc cttgcccctg gccggtaccc atttggcgcc gattcttttc ttgcccccg   1200 gccggccgct cgctcgcctt tggattcttc caaagccgct gatgggatgg tggcgaacac   1260
acccaccacc cgtcttgcc caaagcgacc cggcacaggc cgcgccggct tcactaacca   1320
ctagcgcttg tactaataaa atggtttcta gcgtttgttg ctctccttt tcttttttcg    1380 ccggttcttc ggagccgtgt ggacactgga cagcgtccag tccagcaggc atagggtggt   1440
ctcggcggcg gtcgtccgac gacgatcgat ctccatgaga ttccgcgaca ggccaggacg   1500
gaaagctggg cccttctcac caattcgcgt cggagccgga acaagattcc ctcccccaat   1560
catttcgacg cgccctttct tcgccacccc tcgtggccgt gtttcgcggc cggcccttat   1620
ctccttcccg tgacgcgttc ttttgtagct tagcggccgg cacgttgcta accaggctag   1680
cttcgttcgt ttttaatctg cctatcgaga agagaagaaa aattcgtcca tggggccacg   1740
gcctcttctg caggcatttg gcatgtgaag gaacccgaac cagtgaatgg agatggacgg   1800
atgctgctca gatacgcagt caaacctgcc ggcgaaatta cgggggagc tggctggctg   1860 gctggctgga cgccagatca cacatggatg acgcggcacg cagctagcc gagcaggcgc   1920 tctgcgcacg caagtgtcgt gccgatctcg caccagcagc atcgcgtcct aaacaaagga   1980
ggtcctgtcc tgcac                                                   1995

<210> SEQ ID NO 7
<211> LENGTH: 942
<212> TYPE: DNA
<213> ORGANISM: Zea mays

<400> SEQUENCE: 7
gcactgcact gcactgcacg gatgcagctt tggcaacgag gtgtgtcgcg cagcgctcct     60
gcacggatgt agctttggat tgctggataa tgtctcgcgc aagcgtcgta tttatttatt    120
tatttattac agcctccacc gccgtgcgtg ctccgtttcg gattataata aaactaatat    180
taaataaaaa aatcggatta aaggatgttt ccgaaataaa gatctccacc acaggagcga    240
aagaaaaaaa aagagaaacg ggctatggag aaatggtgtt gcgagtatac ggcggctccg    300
tcgtcgtcgg atcgacatgt acaaagtagg tgcacaaaag gcaaagcaaa atcacctcat    360
caaagaccaa aagcggagca aagaatcgat actaaatcca catgtttttt ttgttcctgt    420
ctactacgtg ctgtgcctgt gcgtgaagca cgattagtac gtgtactcac tcttgtcata    480
```

-continued

```
ttcttttttag tgtcttgtca ctagtcacat ggagtagcaa ccatggctgg cgatacccgc      540
gataaataaa aaaagagag agggagtaat atattagata ctcacccatt ataaattata       600
aaatatttta gagtttgaat aggtagttct tgtatattta tttatagacc ttcaagtttg      660
tccgcctctc gagagccgaa ctttgttgcc catgcttccc cggctcaggt catgccacct      720
ccttcaccaa gggcacacgg aagatctggt ggagcttgtc atcacccgc gcccttcaaa       780 catgtgagga tgcgtcgtcg ctggcactag tagcactcat tgtaggcact acattgacag      840
tttcctccag atatgtagtg aggaaacact tgaacaacac gtttgggatt acatatgatg     900
ttttgtttgt tcatcaatga taattccttc ttcttgctta at                         942
```

<210> SEQ ID NO 8
<211> LENGTH: 6432
<212> TYPE: DNA
<213> ORGANISM: Artificial Sequence
<220> FEATURE:
<223> OTHER INFORMATION: Z. mays, S. pyogenes, Agrobacterium tumefaciens

<400> SEQUENCE: 8

```
ctgcagtgca gcgtgacccg gtcgtgcccc tctctagaga taatgagcat tgcatgtcta      60
agttataaaa aattaccaca tattttttt gtcacacttg tttgaagtgc agtttatcta      120
tctttataca tatatttaaa ctttactcta cgaataatat aatctatagt actacaataa     180
tatcagtgtt ttagagaatc atataaatga acagttagac atggtctaaa ggacaattga     240
gtattttgac aacaggactc tacagtttta tcttttttagt gtgcatgtgt tctccttttt     300
ttttgcaaat agcttcacct atataatact tcatccattt tattagtaca tccatttagg     360
gtttagggtt aatggttttt atagactaat ttttttagta catctatttt attctatttt     420
agcctctaaa ttaagaaaac taaaactcta tttagtttt tttatttaat aatttagata     480
taaaatagaa taaaataaag tgactaaaaa ttaaacaaat acccctttaag aaattaaaaa    540 aactaaggaa acatttttct tgtttcgagt agataatgcc agcctgttaa acgccgtcga     600
cgagtctaac ggacaccaac cagcgaacca gcagcgtcgc gtcgggccaa gcgaagcaga     660
cggcacggca tctctgtcgc tgcctctgga cccctctcga gagttccgct ccaccgttgg     720
acttgctccg ctgtcggcat ccagaaattg cgtggcggag cggcagacgt gagccggcac     780
ggcaggcggc ctcctcctcc tctcacggca ccggcagcta cggggattc ctttcccacc      840 gctccttcgc tttcccttcc tcgcccgccg taataaatag acacccctc cacaccctct      900 ttccccaacc tcgtgttgtt cggagcgcac acacacaa ccagatctcc cccaaatcca       960
cccgtcggca cctccgcttc aaggtacgcc gctcgtcctc cccccccccc cctctctacc     1020
ttctctagat cggcgttccg gtccatggtt agggcccggt agttctactt ctgttcatgt     1080
ttgtgttaga tccgtgtttg tgttagatcc gtgctgctag cgttcgtaca cggatgcgac     1140
ctgtacgtca gacacgttct gattgctaac ttgccagtgt ttctcttgg ggaatcctgg      1200 gatggctcta gccgttccgc agacgggatc gatttcatga tttttttgt ttcgttgcat      1260 agggtttggt ttgccctttt cctttatttc aatatatgcc gtgcacttgt ttgtcgggtc     1320
atcttttcat gcttttttt gtcttggttg tgatgatgtg gtctggttgg gcggtcgttc      1380
tagatcggag tagaattctg tttcaaacta cctggtggat ttattaattt tggatctgta     1440
tgtgtgtgcc atacatattc atagttacga attgaagatg atggatggaa atatcgatct     1500
aggataggta tacatgttga tgcgggtttt actgatgcat atacagagat gcttttttgtt    1560 cgcttggttg tgatgatgtg gtgtggttgg gcggtcgttc attcgttcta gatcggagta    1620
```

-continued

```
gaatactgtt tcaaactacc tggtgtattt attaattttg aactgtatg tgtgtgtcat   1680
acatcttcat agttacgagt ttaagatgga tggaaatatc gatctaggat aggtatacat   1740
gttgatgtgg gttttactga tgcatataca tgatggcata tgcagcatct attcatatgc   1800
tctaaccttg agtacctatc tattataata aacaagtatg ttttataatt attttgatct   1860
tgatatactt ggatgatggc atatgcagca gctatatgtg gatttttta gccctgcctt    1920
catacgctat ttatttgctt ggtactgttt cttttgtcga tgctcaccct gttgtttggt   1980
gttacttctg cagcggccgc tcatatggac aagaagtaca gcatcggcct ggacatcggc   2040
accaacagcg tgggctgggc cgtgatcacc gacgagtaca aggtgccgag caagaagttc   2100
aaggtgctgg gcaacaccga caggcacagc atcaagaaga acctgatcgg cgccctgctg   2160
ttcgacagcg gcgagaccgc cgaggccacc aggctgaaga ggaccgccag gaggaggtac   2220
accaggagga agaacaggat ctgctacctg caggagatct cagcaacga gatggccaag    2280
gtggacgaca gcttcttcca caggctggag agagcttcc tggtggagga ggacaagaag    2340
cacgagaggc acccgatctt cggcaacatc gtggacgagg tggcctacca cgagaagtac   2400
ccgaccatct accacctgag gaagaagctg gtggacagca ccgacaaggc cgacctgagg   2460
ctgatctacc tggccctggc ccacatgatc aagttcaggg gccacttcct gatcgagggc   2520
gacctgaacc cggacaacag cgacgtggac aagctgttca tccagctggt gcagacctac   2580
aaccagctgt tcgaggagaa cccgatcaac gccagcggcg tggacgccaa ggccatcctg   2640
agcgccaggc tgagcaagag caggaggctg gagaacctga tcgcccagct gccgggcgag   2700
aagaagaacg gcctgttcgg caacctgatc gccctgagcc tgggcctgac cccgaacttc   2760
aagagcaact tcgacctggc cgaggacgcc aagctgcagc tgagcaagga cacctacgac   2820
gacgacctgg acaacctgct ggcccagatc ggcgaccagt acgccgacct gttcctggcc   2880
gccaagaacc tgagcgacgc catcctgctg agcgacatcc tgagggtgaa caccgagatc   2940
accaaggccc cgctgagcgc cagcatgatc aagaggtacg acgagcacca ccaggacctg   3000
accctgctga aggccctggt gaggcagcag ctgccggaga agtacaagga gatcttcttc   3060
gaccagagca agaacggcta cgccggctac atcgacggcg cgccagcca ggaggagttc    3120
tacaagttca tcaagccgat cctggagaag atggacggca ccgaggagct gctggtgaag   3180
ctgaacaggg aggacctgct gaggaagcag aggaccttcg acaacggcag catcccgcac   3240
cagatccacc tgggcgagct gcacgccatc ctgaggaggc aggaggactt ctacccgttc   3300
ctgaaggaca cagggagaa gatcgagaag atcctgacct tccgcatccc gtactacgtg    3360
ggcccgctgg ccaggggcaa cagcaggttc gcctggatga ccaggaagag cgaggagacc   3420
atcacccgt ggaacttcga ggaggtggtg acaagggcg ccagcgccca gagcttcatc     3480
gagaggatga ccaacttcga caagaacctg ccgaacgaga aggtgctgcc gaagcacagc   3540
ctgctgtacg agtacttcac cgtgtacaac gagctgacca aggtgaagta cgtgaccgag   3600
ggcatgagga agccggcctt cctgagcggc gagcagaaga aggccatcgt ggacctgctg   3660
ttcaagacca acaggaaggt gaccgtgaag cagctgaagg aggactactt caagaagatc   3720
gagtgcttcg acagcgtgga gatcagcggc gtggaggaca ggttcaacgc cagcctgggc   3780
acctaccacg acctgctgaa gatcatcaag gacaaggact tcctggacaa cgaggagaac   3840
gaggacatcc tggaggacat cgtgctgacc ctgaccctgt tcgaggacag ggagatgatc   3900
gaggagaggc tgaagaccta cgcccacctg ttcgacgaca aggtgatgaa gcagctgaag   3960
```

-continued

```
aggaggaggt acaccggctg gggcaggctg agcaggaagc tgatcaacgg catcagggac    4020
aagcagagcg gcaagaccat cctggacttc ctgaagagcg acggcttcgc caacaggaac    4080
ttcatgcagc tgatccacga cgacagcctg accttcaagg aggacatcca gaaggcccag    4140
gtgagcggcc agggcgacag cctgcacgag cacatcgcca acctggccgg cagcccggcc    4200
atcaagaagg gcatcctgca gaccgtgaag gtggtggacg agctggtgaa ggtgatgggc    4260
aggcacaagc cggagaacat cgtgatcgag atggccaggg agaaccagac cacccagaag    4320
ggccagaaga cagcaggga ggatgaag aggatcgagg agggcatcaa ggagctgggc    4380
agccagatcc tgaaggagca cccggtggag aacacccagc tgcagaacga gaagctgtac    4440
ctgtactacc tgcagaacgg cagggacatg tacgtggacc aggagctgga catcaacagg    4500
ctgagcgact acgacgtgga ccacatcgtg ccgcagagct tcctgaagga cgacagcatc    4560
gacaacaagg tgctgaccag gagcgacaag aacaggggca gagcgacaa cgtgccgagc    4620
gaggaggtgg tgaagaagat gaaaaactac tggaggcagc tgctgaacgc caagctgatc    4680
acccagagga agttcgacaa cctgaccaag gccgagaggg gcggcctgag cgagctggac    4740
aaggccggct tcattaaaag gcagctggtg gagaccaggc agatcaccaa gcacgtggcc    4800
cagatcctgg acagcaggat gaacaccaag tacgacgaga cgacaagct gatcagggag    4860
gtgaaggtga tcacccctgaa gagcaagctg gtgagcgact tcaggaagga cttccagttc    4920
tacaaggtga gggagatcaa taattaccac cacgcccacg acgcctacct gaacgccgtg    4980
gtgggcaccg ccctgattaa aaagtacccg aagctggaga gcgagttcgt gtacggcgac    5040
tacaaggtgt acgacgtgag gaagatgatc gccaagagcg agcaggagat cggcaaggcc    5100
accgccaagt acttcttcta cagcaacatc atgaacttct tcaagaccga gatcaccctg    5160
gccaacggcg agatcaggaa gaggccgctg atcgagacca cggcgagac cggcgagatc    5220
gtgtgggaca agggcaggga cttcgccacc gtgaggaagg tgctgtccat gccgcaggtg    5280
aacatcgtga gaagaccga ggtgcagacc ggcggcttca gcaaggagag catcctgccg    5340
aagaggaaca gcgacaagct gatcgccagg aagaaggact gggacccgaa gaagtacggc    5400
ggcttcgaca cccgaccgt ggcctacagc gtgctggtgg tggccaaggt ggagaagggc    5460
aagagcaaga gctgaagag cgtgaaggag ctggtgggca tcaccatcat ggagaggagc    5520
agcttcgaga gaacccagt ggacttcctg gaggccaagg gctacaagga ggtgaagaag    5580
gacctgatca ttaaactgcc gaagtacagc ctgttcgagc tggagaacgg caggaagagg    5640
atgctggcca cgccggcga gctgcagaag ggcaacgagc tggccctgcc gagcaagtac    5700
gtgaacttcc tgtacctggc cagccactac gagaagctga agggcagccc ggaggacaac    5760
gagcagaagc agctgttcgt ggagcagcac aagcactacc tggacgagat catcgagcag    5820
atcagcgagt tcagcaagag ggtgatcctg gccgacgcca acctggacaa ggtgctgagc    5880
gcctacaaca gcacaggga caagccgatc agggagcagg ccgagaacat catccacctg    5940
ttcaccctga ccaacctggg cgccccggcc gccttcaagt acttcgacac caccatcgac    6000
aggaagaggt acaccagcac caaggaggtg ctggacgcca ccctgatcca ccagagcatc    6060
accgccctgt acgagaccag gatcgacctg agccagctgg cgcgcgacag cagcccgccg    6120
aagaagaaga ggaaggtgag ctggaaggac gccagcggct ggagcaggat gtgaagcttg    6180
atcgttcaaa catttggcaa taaagttttct taagattgaa tcctgttgcc ggtcttgcga    6240
tgattatcat ataatttctg ttgaattacg ttaagcatgt aataattaac atgtaatgca    6300
tgacgttatt tatgagatgg gttttttatga ttagagtccc gcaattatac atttaatacg    6360
```

```
cgatagaaaa caaaatatag cgcgcaaact aggataaatt atcgcgcgcg gtgtcatcta    6420
tgttactaga tc                                                        6432

<210> SEQ ID NO 9
<211> LENGTH: 480
<212> TYPE: DNA
<213> ORGANISM: Artificial Sequence
<220> FEATURE:
<223> OTHER INFORMATION: Oryza sativa, Z. mays, S. pyogenes

<400> SEQUENCE: 9
gggatcttta aacatacgaa cagatcactt aaagttcttc tgaagcaact taaagttatc     60
aggcatgcat ggatcttgga ggaatcagat gtgcagtcag ggaccatagc acaggacagg    120
cgtcttctac tggtgctacc agcaaatgct ggaagccggg aacactgggt acgttggaaa    180
ccacgtgatg tggagtaaga taaactgtag gagaaaagca tttcgtagtg gccatgaag    240 cctttcagga catgtattgc agtatgggcc ggcccattac gcaattggac gacaacaaag    300
actagtatta gtaccacctc ggctatccac atagatcaaa gctggtttaa aagagttgtg    360
cagatgatcc gtggcagtgc agtgcagtgc aggacgtttt agagctagaa atagcaagtt    420
aaaataaggc tagtccgtta tcaacttgaa aaagtggcac cgagtcggtg cttttttttt    480

<210> SEQ ID NO 10
<211> LENGTH: 670
<212> TYPE: DNA
<213> ORGANISM: Artificial Sequence
<220> FEATURE:
<223> OTHER INFORMATION: O. sativa, Z. mays, E. coli, S. pyogenes

<400> SEQUENCE: 10
gggatcttta aacatacgaa cagatcactt aaagttcttc tgaagcaact taaagttatc     60
aggcatgcat ggatcttgga ggaatcagat gtgcagtcag ggaccatagc acaggacagg    120
cgtcttctac tggtgctacc agcaaatgct ggaagccggg aacactgggt acgttggaaa    180
ccacgtgatg tggagtaaga taaactgtag gagaaaagca tttcgtagtg gccatgaag    240 cctttcagga catgtattgc agtatgggcc ggcccattac gcaattggac gacaacaaag    300
actagtatta gtaccacctc ggctatccac atagatcaaa gctggtttaa aagagttgtg    360
cagatgatcc gtggcagtgc agtgcagtgc aggacgtttt agagctagaa atagcaagtt    420
aaaataaggc tagtccgtta tcaacttgaa aaagtggcac cgagtcggtg cacgggctgc    480
agcaggctca cgatctcgct gaactcgcgg aaggcgttca tggccaggaa gggggtcagg    540
gcgaacacca gctcgggctt gtggttgggg tccttgtagt tgcgctcggc ggcgtccatg    600
gggatgccgg cggcgttctc cttggcgaag ccgatctcgc tgttgtgctt gttggggtgc    660
atttttttt                                                            670

<210> SEQ ID NO 11
<211> LENGTH: 6454
<212> TYPE: DNA
<213> ORGANISM: Artificial Sequence
<220> FEATURE:
<223> OTHER INFORMATION: Z. mays, E. coli, A. tumefaciens

<400> SEQUENCE: 11
aacgagaata atgtcgtcat cttcgacctc gacggcggta cctttgacgt cgcgctccgg     60
cggctaagga ccgcactgcc gacgagggca tgagtggcgc cgagatggaa gagaagagga    120
```

```
gcacaaatgg cggtcgtcgg caaagacaaa gagaactcga gcgtgagtgg aggaaggggc    180
aaatgtgtaa ctccagcttg gatatgactc cactgaccag attacgagcg acatcaacta    240
gattgtgtgt ctcagtggct cagtgccatt ttttgaggtt tgggtgccaa tattttttcg    300
tagtggaagg caccgcgccc atcgggtttt gggagccaaa cgccaaaccc gctcgcctca    360
tattccgcaa cgtacagcgg tttcatgggc tggttgaagg cccgggccgc aaaccaaccg    420
agtcgggccg acgccctggg agatccgcac ggctggtctg gcccaagcaa cctggtgggt    480
tggtgccagg ttacagcctg gctgatctg tggacggtgg accatgcaag gttgtactgg    540
gcttgcaagg ttgtactggg cctactggaa cagtcatagc ccgtgccgtc gtggtgaccg    600
tcgtacgcgg ccgatctggc agactgggca ggtcgctgct ccgtgctgtt tgtggatgca    660
atgcaactat gcaagagtga tcacggaaaa cggacggagc ctgtctgtcc tgttgcgacg    720
tagtacaagc gcctgaacag tgacgctacg ctatgccacg agcctacgag tggtaggtag    780
tagtacactg gtcagaatcc agcagtgcac ccacgccgct gctgactttg ctgatgagag    840
ggaggggtcg agcgagtctg tgtgaaaccg tgaaccccgc cggggccttc agtacgtacg    900
ataccacgag cagtagaaaa acaacgccaa agatggcaga gtcaacaacc gatcacagta    960
cgtatcgcat tcacatcaag atttaagaa cgaccccgg ctggccaatg gcaggccact    1020
tggttgcccg tgcccgacag agggacacgg cgccatgccc tccgcgccgc acggacgagg   1080
tgtcgtgaga accggcaaaa aaaaaaatca tcgcaagtgc gctgaagtga agtgccttcc   1140
cccgcgtttc cttgcccctg gccggtaccc atttggcgcc gattcttttc ttgcccccg    1200 gccggccgct cgctcgcctt tggattcttc caaagccgct gatgggatgg tggcgaacac   1260
acccaccacc cgtctttgcc caaagcgacc cggcacaggc cgcgccggct tcactaacca   1320
ctagcgcttt tactaataaa atggtttcta gcgtttgttg ctctccttt tcttttttcg    1380 ccggttcttc ggagccgtgt ggacactgga cagcgtccag tccagcaggc atagggtggt   1440
ctcggcggcg gtcgtccgac gacgatcgat ctccatgaga ttccgcgaca ggccaggacg   1500
gaaagctggg cccttctcac caattcgcgt cggagccgga acaagattcc ctcccccaat   1560
catttcgacg cgccctttct tcgccacccc tcgtggccgt gtttcgcggc cggcccttat   1620
ctccttcccg tgacgcgttc ttttgtagct tagcggccgg cacgttgcta accaggctag   1680
cttcgttcgt ttttaatctg cctatcgaga agagaagaaa aattcgtcca tggggccacg   1740
gcctcttctg caggcatttg gcatgtgaag gaacccgaac cagtgaatgg agatggacgg   1800
atgctgctca gatacgcagt caaacctgcc ggcgaaatta cggggggagc tggctggctg   1860
gctggctgga cgccagatca cacatggatg acgcggcacg gcagctagcc gagcaggcgc   1920
tctgcgcacg caagtgtcgt gccgatctcg caccagcagc atcgcgtcct aaacaaagga   1980
ggtcctgtcc tgcacctagg gttaggcgcg ccggaccggt acctgcagtg cagcgtgacc   2040
cggtcgtgcc cctctctaga gataatgagc attgcatgtc taagttataa aaaattacca   2100 catattttt ttgtcacact tgtttgaagt gcagtttatc tatctttata catatattta    2160
aactttactc tacgaataat ataatctata gtactacaat aatatcagtg ttttagagaa   2220
tcatataaat gaacagttag acatggtcta aaggacaatt gagtattttg acaacaggac   2280
tctacagttt tatcttttta gtgtgcatgt gttctccttt tttttgcaa atagcttcac    2340 ctatataata cttcatccat tttattagta catccattta gggtttaggg ttaatggttt   2400
ttatagacta attttttttag tacatctatt ttattctatt ttagcctcta aattaagaaa   2460
actaaaactc tattttagtt tttttatta ataatttaga tataaaatag aataaaataa    2520
```

-continued

```
agtgactaaa aattaaacaa atacccttta agaaattaaa aaaactaagg aaacattttt    2580
cttgtttcga gtagataatg ccagcctgtt aaacgccgtc gacgagtcta acggacacca    2640
accagcgaac cagcagcgtc gcgtcgggcc aagcgaagca gacggcacgg catctctgtc    2700
gctgcctctg gaccctctc gagagttccg ctccaccgtt ggacttgctc cgctgtcggc     2760
atccagaaat tgcgtggcgg agcggcagac gtgagccggc acggcaggcg gcctcctcct    2820
cctctcacgg caccggcagc tacgggggat tcctttccca ccgctccttc gctttccctt    2880
cctcgcccgc cgtaataaat agacaccccc tccacaccct cttttcccaa cctcgtgttg    2940
ttcggagcgc acacacacac aaccagatct cccccaaatc cacccgtcgg cacctccgct    3000
tcaaggtacg ccgctcgtcc tccccccccc cccctctcta ccttctctag atcggcgttc    3060
cggtccatgg ttagggcccg gtagttctac ttctgttcat gtttgtgtta gatccgtgtt    3120
tgtgttagat ccgtgctgct agcgttcgta cacggatgcg acctgtacgt cagacacgtt    3180
ctgattgcta acttgccagt gtttctcttt ggggaatcct gggatggctc tagccgttcc    3240
gcagacggga tcgatttcat gattttttt gtttcgttgc atagggtttg gtttgccctt     3300
ttcctttatt tcaatatatg ccgtgcactt gttttgtcggg tcatcttttc atgcttttt    3360
ttgtcttggt tgtgatgatg tggtctggtt gggcggtcgt tctagatcgg agtagaattc    3420
tgtttcaaac tacctggtgg atttattaat tttggatctg tatgtgtgtg ccatacatat    3480
tcatagttac gaattgaaga tgatggatgg aaatatcgat ctaggatagg tatacatgtt    3540
gatgcgggtt ttactgatgc atatacagag atgcttttg ttcgcttggt tgtgatgatg     3600
tggtgtggtt gggcggtcgt tcattcgttc tagatcggag tagaatactg tttcaaacta    3660
cctggtgtat ttattaattt tggaactgta tgtgtgtgtc atacatcttc atagttacga    3720
gtttaagatg gatggaaata tcgatctagg ataggtatac atgttgatgt gggttttact    3780
gatgcatata catgatggca tatgcagcat ctattcatat gctctaacct tgagtaccta    3840
tctattataa taaacaagta tgttttataa ttattttgat cttgatatac ttggatgatg    3900
gcatatgcag cagctatatg tggatttttt tagccctgcc ttcatacgct atttatttgc    3960
ttggtactgt ttcttttgtc gatgctcacc ctgttgtttg gtgttacttc tgcagggatc    4020
cggcagcagc catgcagaag ctgatcaaca gcgtgcagaa ctacgcctgg ggcagcaaga    4080
ccgcccctgac cgagctgtac ggcatggaga accccagcag ccagcccatg gccgagctgt    4140
ggatgggcgc ccaccccaag agcagcagcc gcgtgcagaa cgccgccggc gacatcgtga    4200
gcctgcgcga cgtgatcgag agcgacaaga gcacctgct gggcgaggcc gtggccaagc     4260
gcttcggcga gctgcccttc ctgttcaagg tgctgtgcgc cgcccagccc ctgagcatcc    4320
aggtgcaccc caacaagcac aacagcgaga tcggcttcgc caaggagaac gccgccggca    4380
tccccatgga cgccgccgag cgcaactaca aggaccccaa ccacaagccc gagctggtgt    4440
tcgccctgac ccccttcctg gccatgaacg ccttccgcga gttcagcgag atcgtgagcc    4500
tgctgcagcc cgtggccggc gcccacccccg ccatcgccca cttcctgcag cagcccgacg    4560
ccgagcgcct gagcgagctg ttcgccagcc tgctgaacat gcagggcgag gagaagagcc    4620
gcgccctggc catcctgaag agcgccctgg acagccagca gggcgagccc tggcagacca    4680
tccgcctgat cagcgagttc taccccgagg acagcggcct gttcagcccc ctgctgctga    4740
acgtggtgaa gctgaacccc ggcgaggcca tgttcctgtt cgccgagacc ccccacgcct    4800
acctgcaggg cgtggccctg gaggtgatgg ccaacagcga caacgtgctg cgcgccggcc    4860
```

```
tgaccccaa gtacatcgac atccccgagc tggtggccaa cgtgaagttc gaggccaagc    4920
ccgccaacca gctgctgacc cagcccgtga agcaggcgc cgagctggac ttccccatcc    4980
ccgtggacga cttcgccttc agcctgcacg acctgagcga caaggagacc accatcagcc    5040
agcagagcgc cgccatcctg ttctgcgtgg agggcgacgc caccctgtgg aagggcagcc    5100
agcagctgca gctgaagccc ggcgagagcg ccttcatcgc cgccaacgag agcccgtga    5160 ccgtgaaggg ccacggccgc ctggcccgcg tgtacaacaa gctgtgatag gagctcgatc    5220
cgtcgacctg cagatcgttc aaacatttgg caataaagtt tcttaagatt gaatcctgtt    5280
gccggtcttg cgatgattat catataattt ctgttgaatt acgttaagca tgtaataatt    5340
aacatgtaat gcatgacgtt atttatgaga tgggttttta tgattagagt cccgcaatta    5400
tacatttaat acgcgataga aaacaaaata tagcgcgcaa actaggataa attatcgcgc    5460
gcggtgtcat ctatgttact agatcggcgc gccatttaaa tggtaccggt ccgcactgca    5520
ctgcactgca cggatgcagc tttggcaacg aggtgtgtcg cgcagcgctc ctgcacggat    5580
gtagctttgg attgctggat aatgtctcgc gcaagcgtcg tatttattta tttatttatt    5640
acagcctcca ccgccgtgcg tgctccgttt cggattataa taaaactaat attaaataaa    5700
aaaatcggat taaggatgt ttccgaaata aagatctcca ccacaggagc gaaagaaaaa    5760
aaaagagaaa cgggctatgg agaaatggtg ttgcgagtat acggcggctc cgtcgtcgtc    5820
ggatcgacat gtacaaagta ggtgcacaaa aggcaaagca aaatcacctc atcaaagacc    5880
aaaagcggag caaagaatcg atactaaatc cacatgtttt ttttgttcct gtctactacg    5940
tgctgtgcct gtgcgtgaag cacgattagt acgtgtactc actcttgtca tattcttttt    6000
agtgtcttgt cactagtcac atggagtagc aaccatggct ggcgatacc gcgataaata    6060 aaaaaaagag agagggagta atatattaga tactcaccca ttataaatta taaaatattt    6120
tagagtttga ataggtagtt cttgtatatt tatttataga ccttcaagtt tgtccgcctc    6180
tcgagagccg aactttgttg cccatgcttc cccggctcag gtcatgccac ctccttcacc    6240
aagggcacac ggaagatctg gtggagcttg tcatcacccc gcgcccttca aacatgtgag    6300
gatgcgtcgt cgctggcact agtagcactc attgtaggca ctacattgac agtttcctcc    6360
agatatgtag tgaggaaaca cttgaacaac acgtttggga ttacatatga tgttttgttt    6420
gttcatcaat gataattcct tcttcttgct taat                                6454

<210> SEQ ID NO 12
<211> LENGTH: 19
<212> TYPE: DNA
<213> ORGANISM: Zea mays

<400> SEQUENCE: 12
cacacctcgt tgccaaagc                                                  19

<210> SEQ ID NO 13
<211> LENGTH: 21
<212> TYPE: DNA
<213> ORGANISM: Zea mays

<400> SEQUENCE: 13
catcgcgtcc taaacaaagg a                                               21

<210> SEQ ID NO 14
<211> LENGTH: 15
<212> TYPE: DNA
<213> ORGANISM: Zea mays
```

```
<400> SEQUENCE: 14
cctgtcctgc actgc                                                        15

<210> SEQ ID NO 15
<211> LENGTH: 17
<212> TYPE: DNA
<213> ORGANISM: Zea mays

<400> SEQUENCE: 15
tgcgcgacac acctcgt                                                      17

<210> SEQ ID NO 16
<211> LENGTH: 21
<212> TYPE: DNA
<213> ORGANISM: Zea mays

<400> SEQUENCE: 16
catcgcgtcc taaacaaagg a                                                 21

<210> SEQ ID NO 17
<211> LENGTH: 23
<212> TYPE: DNA
<213> ORGANISM: Zea mays

<400> SEQUENCE: 17
caaagctgca tccgtgcagt gca                                               23

<210> SEQ ID NO 18
<211> LENGTH: 23
<212> TYPE: DNA
<213> ORGANISM: Zea mays

<400> SEQUENCE: 18
actgttgtca ccgtcccagt cta                                               23

<210> SEQ ID NO 19
<211> LENGTH: 27
<212> TYPE: DNA
<213> ORGANISM: Zea mays

<400> SEQUENCE: 19
gtcctttaga ccatgtctaa ctgttca                                           27

<210> SEQ ID NO 20
<211> LENGTH: 25
<212> TYPE: DNA
<213> ORGANISM: Zea mays

<400> SEQUENCE: 20
cgcgcaaact aggataaatt atcgc                                             25

<210> SEQ ID NO 21
<211> LENGTH: 25
<212> TYPE: DNA
<213> ORGANISM: Zea mays

<400> SEQUENCE: 21
cacatgggct agttgttagc cattg                                             25

<210> SEQ ID NO 22
<211> LENGTH: 42
<212> TYPE: DNA
```

<210> SEQ ID NO 22
<211> LENGTH: 42
<212> TYPE: DNA
<213> ORGANISM: Zea mays

<400> SEQUENCE: 22
cgcggccgtg gcatcgtcgt cacctgggcg ccgcaggagg ag                           42

<210> SEQ ID NO 23
<211> LENGTH: 14
<212> TYPE: PRT
<213> ORGANISM: Zea mays

<400> SEQUENCE: 23

Arg Gly Arg Gly Ile Val Val Ala Trp Ala Pro Gln Glu Glu
1               5                   10

<210> SEQ ID NO 24
<211> LENGTH: 20
<212> TYPE: DNA
<213> ORGANISM: Zea mays

<400> SEQUENCE: 24
ggccgtggca cgtcgtcacc                                                   20

<210> SEQ ID NO 25
<211> LENGTH: 42
<212> TYPE: DNA
<213> ORGANISM: Zea mays

<400> SEQUENCE: 25
ttcttcttgg ggagcccact tcacaactat acctctacct ct                          42

<210> SEQ ID NO 26
<211> LENGTH: 108
<212> TYPE: DNA
<213> ORGANISM: Zea mays

<400> SEQUENCE: 26
cccgacgggg tggaggacga ggtgagaggt agaggtatag ttgtgaagtg ggctccccaa       60
gaagaagtgc tcgcgcaccc ggccgtcggc ggcttcctca cccacaac                   108

<210> SEQ ID NO 27
<211> LENGTH: 84
<212> TYPE: DNA
<213> ORGANISM: Zea mays

<400> SEQUENCE: 27
agaggtagag gtatagttgt gaagtgggct ccccaagaag aaagaggtag aggtatagtt       60
gtgaagtggg ctccccaaga agaa                                              84

<210> SEQ ID NO 28
<211> LENGTH: 14
<212> TYPE: PRT
<213> ORGANISM: Zea mays

<400> SEQUENCE: 28

Arg Gly Arg Gly Ile Val Val Lys Trp Ala Pro Gln Glu Glu
1               5                   10

<210> SEQ ID NO 29
<211> LENGTH: 150
<212> TYPE: DNA
<213> ORGANISM: Zea mays

<400> SEQUENCE: 29

```
accggcgtag tcaccgatct tccagcccct aacgttttca cccatgccga caacgacacc    60
ggcaccttcg tgaccaccga ctaatggtag cttaactggc aatggccagt caccgtgcca   120
agcgtgcaag tcagtgtgac agacaccaga                                   150

<210> SEQ ID NO 30
<211> LENGTH: 256
<212> TYPE: DNA
<213> ORGANISM: Zea mays

<400> SEQUENCE: 30
agccgcggca tcgtcgtcac cgttttagag ctagaaatag caagttaaaa taaggctagt    60
ccgttatcaa cttgaaaaag tggcaccgag tcggtgcacc ggcgtagtca ccgatcttcc   120
agcccttaac gttttcaccc atgccgacaa cgacaccggc accttcgtga ccaccgacta   180
atggtagctt aactggcaat ggccagtcac cgtgccaagc gtgcaagtca gtgtgacaga   240
caccagattt tttttt                                                  256

<210> SEQ ID NO 31
<211> LENGTH: 150
<212> TYPE: DNA
<213> ORGANISM: Zea mays

<400> SEQUENCE: 31
tctggtgtct gtcacactga cttgcacgct tggcacggtg actggccatt gccagttaag    60
ctaccattag tcggtggtca cgaaggtgcc ggtgtcgttg tcggcatggg tgaaaacgtt   120
aagggctgga agatcggtga ctacgccggt                                   150

<210> SEQ ID NO 32
<211> LENGTH: 101
<212> TYPE: DNA
<213> ORGANISM: Zea mays

<400> SEQUENCE: 32
tgtgggtgag gaagccgccg acggccgggt gcgcgagcac ctcctcctgc ggcgcccact    60
tgacgacgat gccacggccg cgcacctcgt cctccacccc g                      101

<210> SEQ ID NO 33
<211> LENGTH: 251
<212> TYPE: DNA
<213> ORGANISM: Zea mays

<400> SEQUENCE: 33
tctggtgtct gtcacactga cttgcacgct tggcacggtg actggccatt gccagttaag    60
ctaccattag tcggtggtca cgaaggtgcc ggtgtcgttg tcggcatggg tgaaaacgtt   120
aagggctgga agatcggtga ctacgccggt tgtgggtgag gaagccgccg acggccgggt   180
gcgcgagcac ctcctcctgc ggcgcccact tgacgacgat gccacggccg cgcacctcgt   240
cctccacccc g                                                       251
```